(12) United States Patent
Kimura

(10) Patent No.: US 11,635,532 B2
(45) Date of Patent: Apr. 25, 2023

(54) RADIATION IMAGING SYSTEM, CAMERA CONTROL APPARATUS, AND CONTROL METHOD

(71) Applicant: CANON KABUSHIKI KAISHA, Tokyo (JP)

(72) Inventor: Tomoki Kimura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 89 days.

(21) Appl. No.: 16/927,749

(22) Filed: Jul. 13, 2020

(65) Prior Publication Data
US 2020/0348426 A1    Nov. 5, 2020

Related U.S. Application Data

(63) Continuation of application No. PCT/JP2018/047698, filed on Dec. 26, 2018.

(30) Foreign Application Priority Data

Jan. 16, 2018    (JP) .............................. JP2018-005096

(51) Int. Cl.
*G01T 1/29*    (2006.01)
*G01T 1/17*    (2006.01)
*H04N 5/32*    (2023.01)

(52) U.S. Cl.
CPC .............. *G01T 1/2978* (2013.01); *G01T 1/17* (2013.01); *H04N 5/32* (2013.01)

(58) Field of Classification Search
CPC ........... G01T 1/2978; G01T 1/17; H04N 5/32; H04N 5/232; A61B 6/00
See application file for complete search history.

(56) References Cited

U.S. PATENT DOCUMENTS 5,334,828 A * 8/1994 Shimoni ................. G01S 17/06
356/400
6,327,331 B1 * 12/2001 Toth ......................... A61B 6/08
378/207

(Continued)

FOREIGN PATENT DOCUMENTS

CN    105310707 A    2/2016
CN    107077745 A    8/2017

(Continued)

*Primary Examiner* — David P Porta
*Assistant Examiner* — Djura Malevic
(74) *Attorney, Agent, or Firm* — Canon U.S.A., Inc. IP Division

(57) ABSTRACT

There is provided a mechanism that enables a camera apparatus to record an appropriate video image relating to circumstances in which radiation imaging is performed in an imaging room. A radiation imaging system includes a radiation generating apparatus configured to generate radiation toward an object, a radiation detecting apparatus configured to detect, as an image signal, the radiation incident thereto, a camera apparatus configured to record a video image relating to circumstances in which radiation imaging is performed using the radiation in an imaging room, and a camera control apparatus configured to control the camera apparatus. The camera control apparatus recognizes an imaging location at which the radiation imaging is performed in the imaging room, and sets a parameter of the camera apparatus in accordance with the recognized imaging location.

16 Claims, 19 Drawing Sheets

(56) References Cited

U.S. PATENT DOCUMENTS

| | | | | |
|---|---|---|---|---|
| 7,333,497 B2* | 2/2008 | Nishiyama | H04N 21/6377 | 370/395.6 |
| 7,348,974 B2* | 3/2008 | Smith | G06T 7/80 | 378/57 |
| 7,860,285 B2* | 12/2010 | Kariathungal | G16H 30/40 | 382/128 |
| 7,889,906 B2* | 2/2011 | Smith | A61N 5/1049 | 382/294 |
| 8,502,876 B2* | 8/2013 | Wang | G10L 15/26 | 348/222.1 |
| 8,724,772 B2* | 5/2014 | Nishii | G01N 23/043 | 378/42 |
| 9,097,643 B2* | 8/2015 | Tsuchiya | A61B 6/54 | |
| 9,532,756 B2* | 1/2017 | Wakai | A61B 5/742 | |
| 9,734,419 B1* | 8/2017 | Ye | G06T 7/85 | |
| 9,778,037 B2 | 10/2017 | Bestler | G01C 15/008 | |
| 9,903,825 B2* | 2/2018 | Nishii | A61B 6/487 | |
| 10,315,054 B2* | 6/2019 | Mead | H04N 13/204 | |
| 10,702,229 B2* | 7/2020 | Lee | A61B 6/587 | |
| 10,828,512 B2* | 11/2020 | Meir | G16H 30/40 | |
| 10,926,106 B2* | 2/2021 | Berlinger | G06T 7/337 | |
| 10,974,074 B2* | 4/2021 | Hale | A61N 5/1075 | |
| 11,096,759 B2* | 8/2021 | Spahn | G16H 40/63 | |
| 11,110,301 B2* | 9/2021 | Yang | A61N 5/1075 | |
| 2002/0085668 A1* | 7/2002 | Blumhofer | A61N 5/1049 | 378/68 |
| 2003/0038015 A1* | 2/2003 | Rosello | G07D 7/12 | 194/207 |
| 2003/0043962 A1* | 3/2003 | Lai | G01N 23/046 | 378/23 |
| 2005/0069089 A1* | 3/2005 | Armstrong | A61B 6/587 | 378/162 |
| 2005/0135344 A1* | 6/2005 | Nishiyama | H04N 21/41407 | 370/352 |
| 2006/0036170 A1* | 2/2006 | Lachaine | G01S 7/5205 | 600/437 |
| 2006/0079757 A1* | 4/2006 | Smith | G06T 7/80 | 600/416 |
| 2006/0122502 A1* | 6/2006 | Scherch | A61N 5/1049 | 600/426 |
| 2006/0215813 A1* | 9/2006 | Scherch | A61N 5/1049 | 378/65 |
| 2009/0022383 A1* | 1/2009 | Falco | A61N 5/1049 | 378/65 |
| 2009/0052760 A1* | 2/2009 | Smith | G06T 7/593 | 382/132 |
| 2009/0187112 A1* | 7/2009 | Meir | A61B 5/0077 | 600/595 |
| 2009/0285357 A1* | 11/2009 | Khamene | A61B 6/5217 | 378/207 |
| 2010/0259624 A1* | 10/2010 | Li | G06T 7/80 | 348/E17.002 |
| 2011/0085645 A1* | 4/2011 | Paidi | A61B 6/584 | 378/207 |
| 2012/0128129 A1* | 5/2012 | Nishii | A61B 6/5205 | 378/98 |
| 2012/0132810 A1* | 5/2012 | Uchiyama | H04N 5/361 | 250/370.08 |
| 2012/0243663 A1* | 9/2012 | Nishii | A61B 6/4233 | 378/98 |
| 2012/0312961 A1* | 12/2012 | Raleigh | A61B 6/542 | 250/206 |
| 2012/0321047 A1* | 12/2012 | Iwase | G01T 1/243 | 378/114 |
| 2013/0022901 A1* | 1/2013 | Buurman | H05G 2/008 | 430/30 |
| 2013/0114793 A1* | 5/2013 | Ohta | A61B 6/588 | 378/63 |
| 2013/0170617 A1* | 7/2013 | Tsuchiya | A61B 6/54 | 378/62 |
| 2013/0229495 A1* | 9/2013 | Bani-Hashemi | A61B 6/582 | 348/46 |
| 2014/0084168 A1* | 3/2014 | Duraj | G01T 1/2006 | 250/361 R |
| 2014/0131564 A1* | 5/2014 | Duraj | G01V 5/06 | 250/361 R |
| 2014/0233704 A1* | 8/2014 | Nishii | A61B 6/5205 | 378/98 |
| 2014/0313347 A1* | 10/2014 | Wu | G06T 7/80 | 348/187 |
| 2014/0321614 A1* | 10/2014 | Yamada | A61B 6/464 | 378/62 |
| 2015/0078523 A1* | 3/2015 | Melman | A61B 6/4028 | 378/62 |
| 2015/0085072 A1* | 3/2015 | Yan | G01S 17/48 | 348/43 |
| 2015/0098075 A1* | 4/2015 | Bestler | G01S 7/4817 | 356/3.01 |
| 2015/0105976 A1* | 4/2015 | Shikii | B60H 1/00742 | 701/36 |
| 2015/0168566 A1* | 6/2015 | Shikino | H04N 5/32 | 250/394 |
| 2015/0182761 A1* | 7/2015 | Thomson | A61B 5/055 | 600/407 |
| 2015/0352376 A1* | 12/2015 | Wiggers | A61N 5/1075 | 378/207 |
| 2016/0029986 A1* | 2/2016 | Nishii | A61B 6/4233 | 250/394 |
| 2017/0055925 A1* | 3/2017 | Lee | A61B 6/587 | |
| 2017/0209714 A1* | 7/2017 | Bennett | A61N 5/1069 | |
| 2018/0232910 A1* | 8/2018 | Mead | G06T 5/006 | |
| 2018/0345040 A1* | 12/2018 | Meir | H04N 13/282 | |
| 2019/0129045 A1* | 5/2019 | Mellor | G01T 7/00 | |
| 2020/0262908 A1* | 8/2020 | Jones | A61P 29/00 | |
| 2020/0315540 A1* | 10/2020 | Jones | A61B 5/6873 | |
| 2020/0368850 A1* | 11/2020 | Hall | B29C 64/153 | |
| 2020/0375567 A1* | 12/2020 | Kimura | G06K 9/6262 | |
| 2021/0161501 A1* | 6/2021 | Sendai | A61B 6/547 | |

FOREIGN PATENT DOCUMENTS

| | | |
|---|---|---|
| EP | 3096513 A1 | 11/2016 |
| JP | 2003265460 A | 9/2003 |
| JP | 2004041605 A | 2/2004 |
| JP | 2005135344 A | 5/2005 |
| JP | 2006277486 A | 10/2006 |
| JP | 2013153812 A | 8/2013 |
| RU | 2634629 C2 | 11/2017 |
| WO | 2019/142629 A1 | 7/2019 |

* cited by examiner

FIG. 10

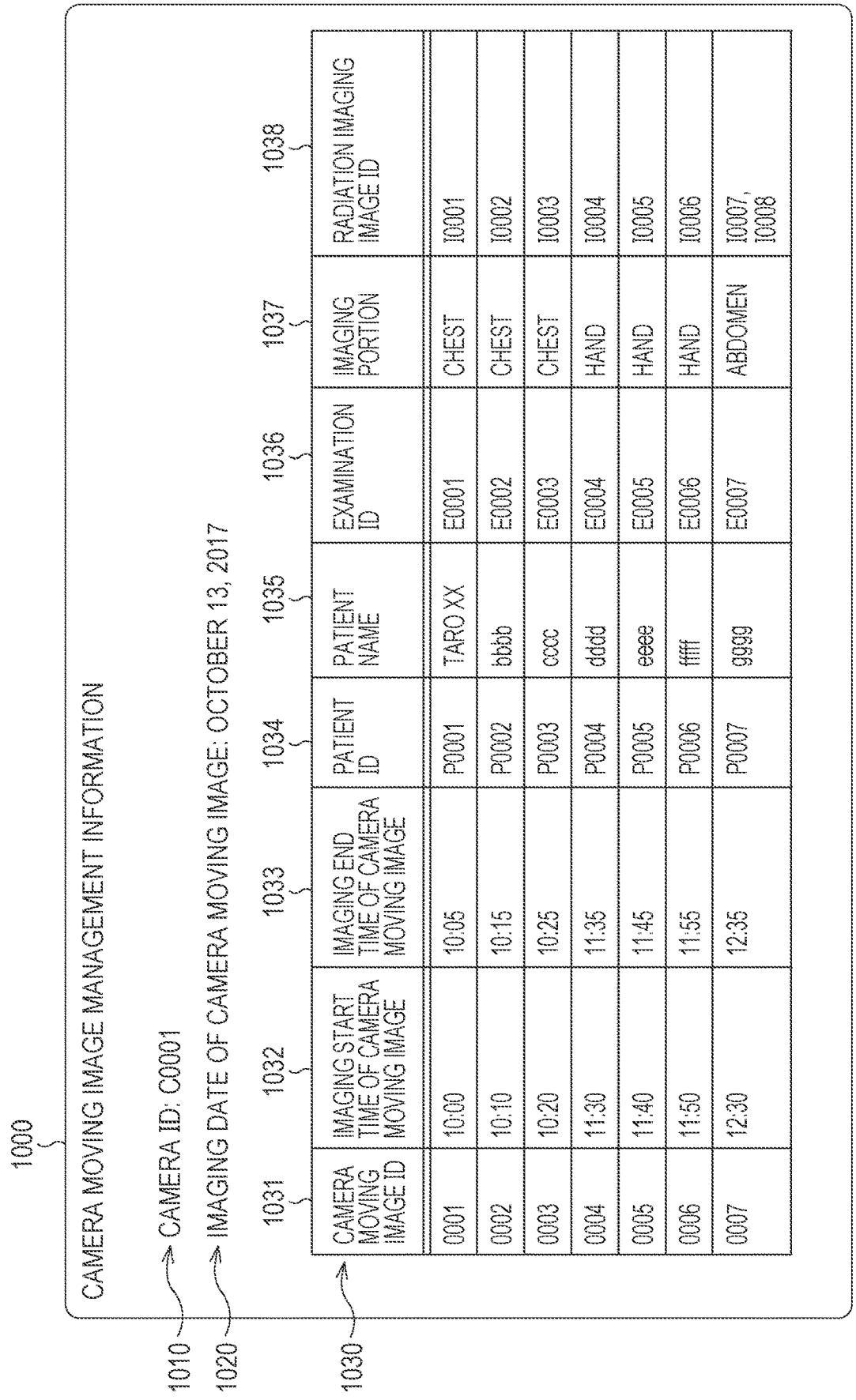

CAMERA MOVING IMAGE MANAGEMENT INFORMATION

1010 → CAMERA ID: C0001
1020 → IMAGING DATE OF CAMERA MOVING IMAGE: OCTOBER 13, 2017

1030

| CAMERA MOVING IMAGE ID (1031) | IMAGING START TIME OF CAMERA MOVING IMAGE (1032) | IMAGING END TIME OF CAMERA MOVING IMAGE (1033) | PATIENT ID (1034) | PATIENT NAME (1035) | EXAMINATION ID (1036) | IMAGING PORTION (1037) | RADIATION IMAGING ID (1038) |
|---|---|---|---|---|---|---|---|
| 0001 | 10:00 | 10:05 | P0001 | TARO XX | E0001 | CHEST | I0001 |
| 0002 | 10:10 | 10:15 | P0002 | bbbb | E0002 | CHEST | I0002 |
| 0003 | 10:20 | 10:25 | P0003 | cccc | E0003 | CHEST | I0003 |
| 0004 | 11:30 | 11:35 | P0004 | dddd | E0004 | HAND | I0004 |
| 0005 | 11:40 | 11:45 | P0005 | eeee | E0005 | HAND | I0005 |
| 0006 | 11:50 | 11:55 | P0006 | ffff | E0006 | HAND | I0006 |
| 0007 | 12:30 | 12:35 | P0007 | gggg | E0007 | ABDOMEN | I0007, I0008 |

| IMAGING PORTION | CAMERA ID |
|---|---|
| CHEST | C0001 |
| HAND | C0002 |

RADIATION IMAGING SYSTEM, CAMERA CONTROL APPARATUS, AND CONTROL METHOD

CROSS-REFERENCE TO RELATED APPLICATIONS

This application is a Continuation of International Patent Application No. PCT/JP2018/047698, filed Dec. 26, 2018, which claims the benefit of Japanese Patent Application No. 2018-005096, filed Jan. 16, 2018, both of which are hereby incorporated by reference herein in their entirety.

BACKGROUND OF THE INVENTION

Field of the Invention

The present invention relates to a radiation imaging system that images an object using radiation, a camera control apparatus included in the radiation imaging system, and a control method for the same.

Background Art

Recently, a camera apparatus has come to be installed in an imaging room at some hospitals for the purposes of grasping the condition of an object during an examination based on radiation imaging and of recording circumstances in which the examination is performed to analyze a cause of a failed image in the radiation imaging. There is a technique of causing a camera apparatus to cooperate with a radiation imaging system and controlling the camera apparatus using information held by the radiation imaging system in such a case. For example, PTL 1 describes a technique of setting in advance an imaging range, an imaging target position, and an imaging direction of a camera apparatus in accordance with circumstances in which an examination is performed and controlling the direction of the camera apparatus in accordance with the progress of the examination.

CITATION LIST

Patent Literature

PTL1: Japanese Patent Laid-Open No. 2003-265460

However, the technique described in PTL 1 does not assume a circumstance in which radiation imaging is performed at various locations in an imaging room since the technique assumes that the positions of a radiation generating apparatus that generates radiation, an object, and a radiation detecting apparatus that detects incident radiation are fixed. In terms of this, depending on the hospital, there may be cases where an imaging table for the standing position and an imaging table for the supine position are provided in an imaging room, and one of these is used in accordance with an examination based on radiation imaging, for example. In such a case, it is difficult to appropriately control the direction of the camera apparatus with the technique described in PTL 1.

The present invention is made in view of such a problem and an object thereof is to provide a mechanism that enables a camera apparatus to record an appropriate video image relating to circumstances in which radiation imaging is performed in an imaging room.

SUMMARY OF THE INVENTION

A radiation imaging system according to the present invention includes a radiation generating apparatus configured to generate radiation toward an object, a radiation detecting apparatus configured to detect the radiation as an image signal, a camera apparatus configured to record a video image relating to radiation imaging performed using the radiation in an imaging room, and a camera control apparatus configured to control the camera apparatus, in which the camera control apparatus includes a recognition unit configured to recognize an imaging location at which the radiation imaging is performed, and a setting unit configured to set a parameter of the camera apparatus in accordance with the imaging location recognized by the recognition unit.

The present invention also encompasses a camera control apparatus included in the radiation imaging system described above, and a control method for the same.

Further features of the present invention will become apparent from the following description of exemplary embodiments with reference to the attached drawings.

BRIEF DESCRIPTION OF THE DRAWINGS

FIG. 10 illustrates the first embodiment of the present invention and is a schematic diagram illustrating an example of camera moving image management information managed by a moving image managing unit of the camera control apparatus illustrated in FIG. 5.

FIG. 15 illustrates the fourth embodiment of the present invention and is a diagram illustrating an example of a correspondence table used by a camera selecting unit illustrated in FIG. 14 to select one of a plurality of camera apparatuses.

DESCRIPTION OF THE EMBODIMENTS

Configurations for embodying the present invention (embodiments) will be described below with reference to the drawings.

First Embodiment

A first embodiment of the present invention will be described first.

Figure 1:
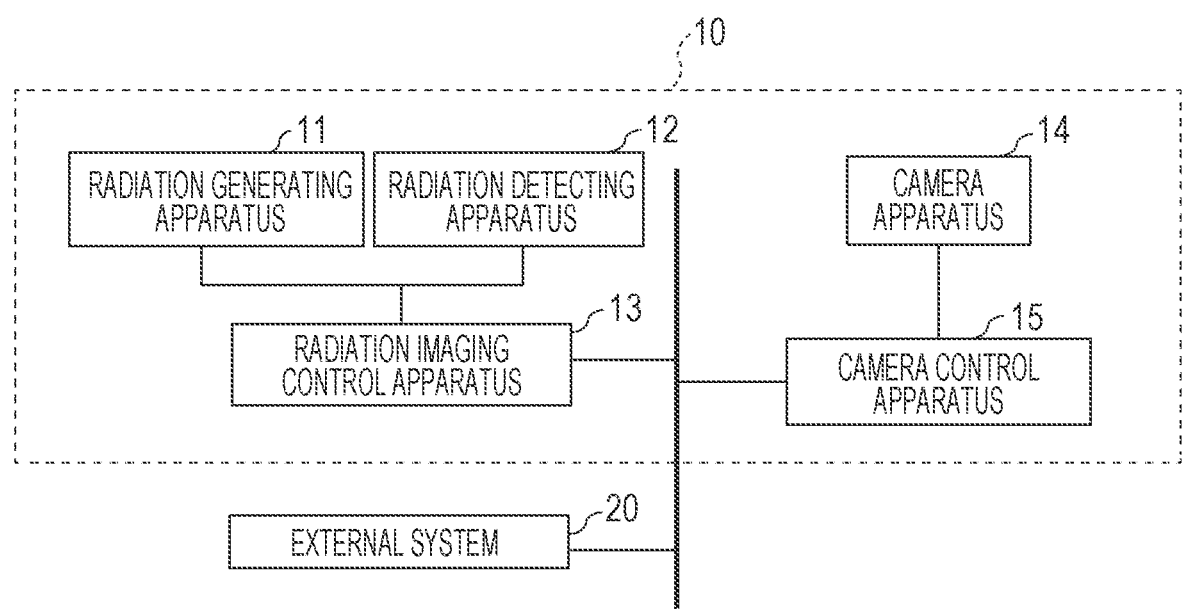
FIG. 1 is a schematic diagram illustrating an example of an overview of a configuration of a radiation imaging system according to a first embodiment of the present invention.

FIG. 1 is a schematic diagram illustrating an example of an overview of a configuration of a radiation imaging system 10 according to the first embodiment of the present invention. As illustrated in FIG. 1, the radiation imaging system 10 according to the first embodiment includes a radiation generating apparatus 11, a radiation detecting apparatus 12, a radiation imaging control apparatus 13, a camera apparatus 14, and a camera control apparatus 15. In addition, as illustrated in FIG. 1, the radiation imaging system 10 according to the first embodiment is configured to be able to cooperate with an external system 20.

The radiation generating apparatus 11 includes a radiation tube that generates radiation. In the case of the present embodiment, the radiation generating apparatus 11 exposes a patient serving as an object to radiation on the basis of control performed by the radiation imaging control apparatus 13. In the present embodiment, radiation is preferably X-rays. However, in the present invention, radiation is not limited to the X-rays, and another kind of radiation, for example, α radiation, β radiation, or γ radiation, may also be used.

The radiation detecting apparatus 12 detects, as an image signal (radiation image signal), radiation that is emitted from the radiation generating apparatus 11 and that is incident thereto, generates a radiation imaging image based on this radiation image signal, and outputs the generated radiation imaging image to the radiation imaging control apparatus 13.

In addition, in the present embodiment, the radiation generating apparatus 11 and the radiation detecting apparatus 12 are appropriately disposed at locations suitable for radiation imaging of an object in an imaging room.

The radiation imaging control apparatus 13 is connected to the radiation generating apparatus 11 and the radiation detecting apparatus 12 with a cable or wirelessly and controls operations of the radiation generating apparatus 11 and the radiation detecting apparatus 12. In addition, the radiation imaging control apparatus 13 performs predetermined image processing on a radiation imaging image output from the radiation imaging control apparatus 13, and performs processing of displaying the radiation imaging image having undergone the image processing or processing of storing data of the radiation imaging image having undergone the image processing. Further, the radiation imaging control apparatus 13 is connected to the external system 20 and the camera control apparatus 15 via a network, and is configured to be able to exchange examination information or the like.

The camera apparatus 14 is an apparatus that records a video image relating to circumstances in which radiation imaging is performed in an imaging room. Specifically, in the present embodiment, the camera apparatus 14 records a moving image as the video image relating to circumstances in which radiation imaging is performed in an imaging room, and also transfers this moving image to the camera control apparatus 15. Hereinafter, this moving image is referred to as a camera moving image.

The camera control apparatus 15 is connected to the camera apparatus 14 with a cable or wirelessly and controls an operation of the camera apparatus 14.

The external system 20 is an external information system that cooperates with the radiation imaging control apparatus 13 and is, for example, a system generally implemented as a RIS (Radiology Information System) in a radiology department.

Figure 2:
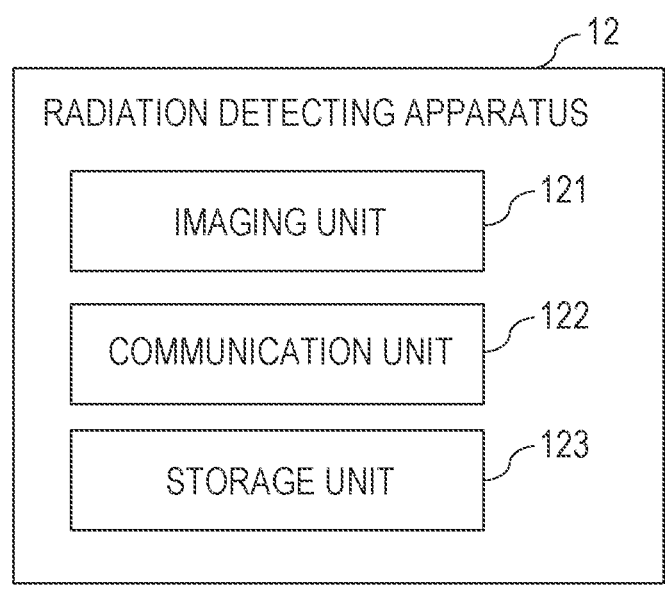
FIG. 2 illustrates the first embodiment of the present invention and is a schematic diagram illustrating an example of a functional configuration of a radiation detecting apparatus illustrated in FIG. 1.

FIG. 2 illustrates the first embodiment of the present invention and is a schematic diagram illustrating an example of a functional configuration of the radiation detecting apparatus 12 illustrated in FIG. 1. As illustrated in FIG. 2, the radiation detecting apparatus 12 includes an imaging unit 121, a communication unit 122, and a storage unit 123.

The imaging unit 121 detects, as an image signal (radiation image signal), radiation that is radiated from the radiation generating apparatus 11 and is incident thereto, and generates a radiation imaging image based on this radiation image signal.

The communication unit 122 performs communication with the radiation imaging control apparatus 13 and performs transmission of the radiation imaging image generated by the imaging unit 121 to the radiation imaging control apparatus 13, for example.

The storage unit 123 stores a program and various kinds of information relating to control of the operation of the radiation detecting apparatus 12. The storage unit 123 also stores data of a radiation imaging image generated by the imaging unit 121 and various kinds of information obtained by performing communication with the radiation imaging control apparatus 13.

Figure 3:
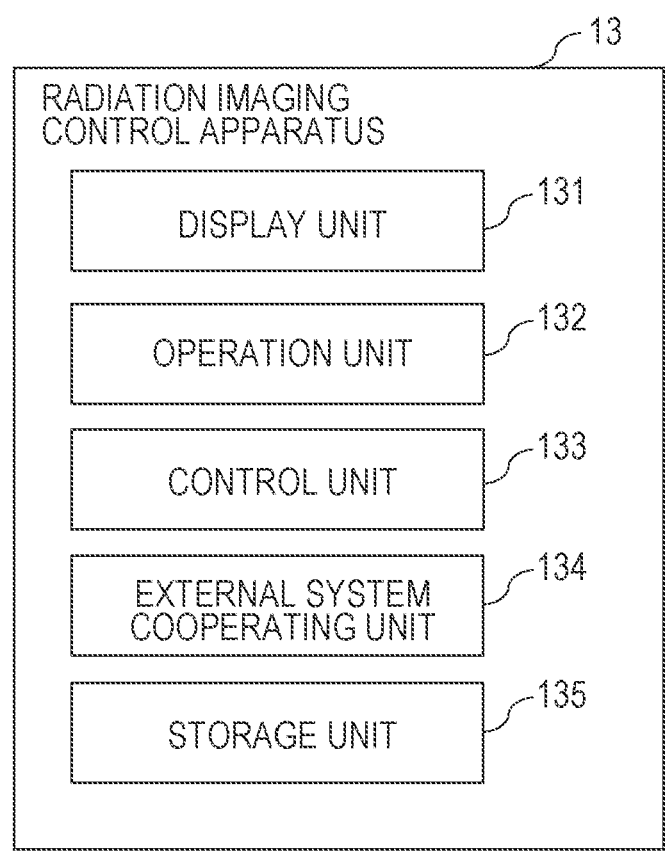
FIG. 3 illustrates the first embodiment of the present invention and is a schematic diagram illustrating an example of a functional configuration of a radiation imaging control apparatus illustrated in FIG. 1.

FIG. 3 illustrates the first embodiment of the present invention and is a schematic diagram illustrating an example of a functional configuration of the radiation imaging control apparatus 13 illustrated in FIG. 1. As illustrated in FIG. 3, the radiation imaging control apparatus 13 includes a display unit 131, an operation unit 132, a control unit 133, an external system cooperating unit 134, and a storage unit 135.

The display unit 131 is constituted by, for example, a liquid crystal display, and displays, to an operator on a screen, examination information, a radiation imaging image obtained by radiation imaging, and so on.

The operation unit 132 is constituted by, for example, a mouse and keyboard, a radiation radiating switch, and various buttons, and accepts input information from the operator.

The control unit 133 controls individual constituent units of the radiation generating apparatus 11, the radiation detecting apparatus 12, and the radiation imaging control apparatus 13 in accordance with an operation performed by the operator on the operation unit 132 to perform control and processing relating to radiation imaging. The control unit 133 also performs processing such as processing of starting and ending radiation imaging, processing of obtaining and storing a radiation imaging image, processing of transmitting information on circumstances in which an examination based on radiation imaging is performed and imaging instruction information to the camera control apparatus 15, and so on.

The external system cooperating unit 134 cooperates with the external system 20, and obtains information relating to radiation imaging such as examination information from the external system 20.

The storage unit 135 stores a program and various kinds of information relating to control of the operation of the radiation imaging control apparatus 13. The storage unit 135 also stores various kinds of information obtained through the control of the operation. Herein, the various kinds of information obtained through the control of the operation include, for example, information obtained from the external system 20, a radiation imaging image obtained from the radiation detecting apparatus 12, and so on.

Figure 4:
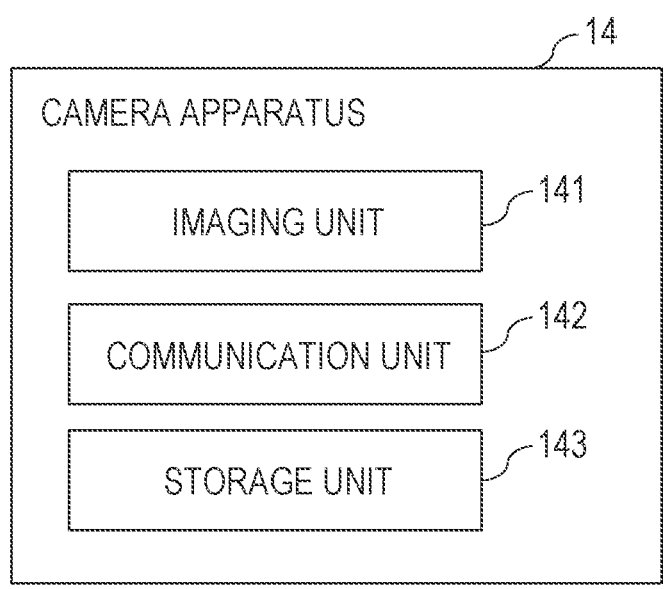
FIG. 4 illustrates the first embodiment of the present invention and is a schematic diagram illustrating an example of a functional configuration of a camera apparatus illustrated in FIG. 1.

FIG. 4 illustrates the first embodiment of the present invention and is a schematic diagram illustrating an example of a functional configuration of the camera apparatus 14 illustrated in FIG. 1. As illustrated in FIG. 4, the camera apparatus 14 includes an imaging unit 141, a communication unit 142, and a storage unit 143.

The imaging unit 141 captures a video image (camera moving image) relating to circumstances in which radiation imaging is performed in an imaging room on the basis of control performed by the camera control apparatus 15.

The communication unit 142 performs communication with the camera control apparatus 15 and performs transmission of a camera moving image obtained by the imaging unit 141 to the camera control apparatus 15, for example.

The storage unit 143 stores a program and various kinds of information relating to control of the operation of the camera apparatus 14. The storage unit 143 also stores data of a camera moving image obtained by the imaging unit 141, various kinds of information obtained by performing communication with the camera control apparatus 15, and so on.

Figure 5:
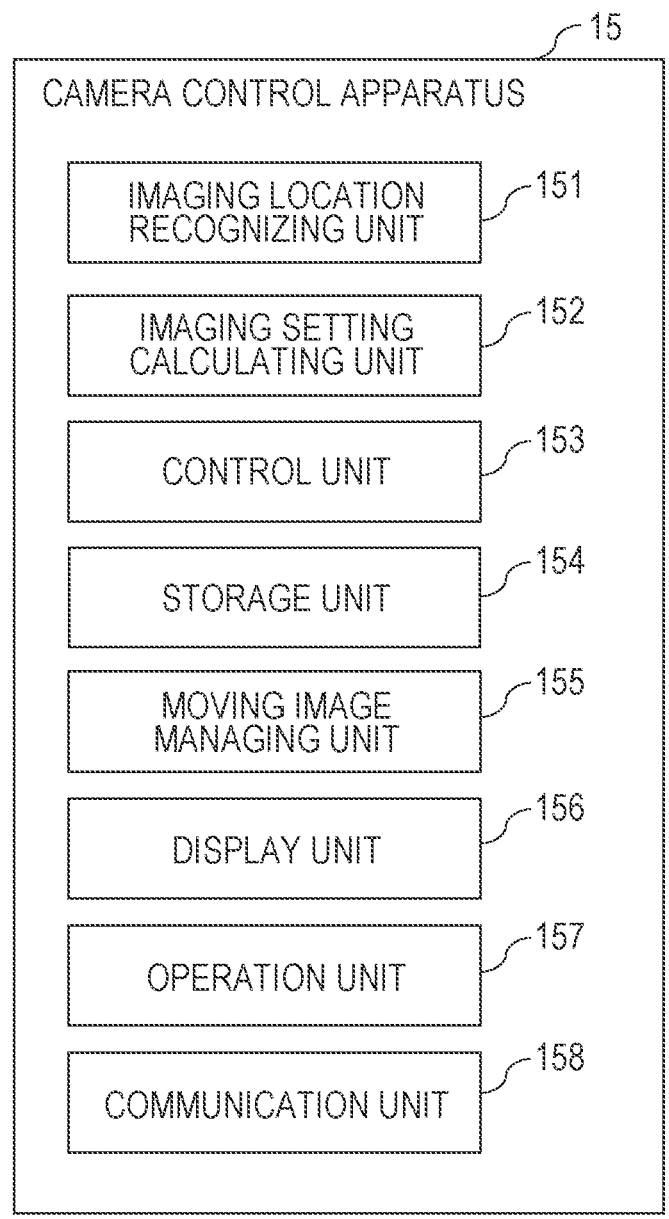
FIG. 5 illustrates the first embodiment of the present invention and is a schematic diagram illustrating an example of a functional configuration of a camera control apparatus illustrated in FIG. 1.

FIG. 5 illustrates the first embodiment of the present invention and is a schematic diagram illustrating an example of a functional configuration of the camera control apparatus 15 illustrated in FIG. 1. As illustrated in FIG. 5, the camera control apparatus 15 includes an imaging location recognizing unit 151, an imaging setting calculating unit (imaging setting unit) 152, a control unit 153, a storage unit 154, a moving image managing unit 155, a display unit 156, an operation unit 157, and a communication unit 158.

The imaging location recognizing unit 151 recognizes an imaging location at which radiation imaging is performed in an imaging room on the basis of information (such as imaging instruction information) transmitted from the radiation imaging control apparatus 13.

The imaging setting calculating unit 152 calculates settings of the camera apparatus 14 in accordance with the imaging location recognized by the imaging location recognizing unit 151. The imaging setting calculating unit 152 calculates, as the settings of the camera apparatus 14, a direction and an imaging magnification of the camera apparatus 14, for example. Note that the control unit 153 may create in advance a table in which the direction and the imaging magnification of the camera apparatus 14 are determined in accordance with the imaging location.

As described above, the imaging setting calculating unit (imaging setting unit) 152 sets parameters of the camera apparatus 14 in accordance with the imaging location recognized by the imaging location recognizing unit 151. The parameters of the camera apparatus 14 include the direction and the imaging magnification of the camera apparatus 14.

For example, the control unit 153 controls individual constituent units of the camera apparatus 14 and the camera control apparatus 15 in accordance with an operation performed by an operator on the operation unit 157 to perform control and processing relating to capturing of a moving image performed by the camera apparatus 14. The control unit 153 also preforms processing such as processing of transmitting, to the camera apparatus 14, the settings of the camera apparatus 14 calculated by the imaging setting calculating unit 152 and instructions to start and end capturing of a moving image performed by the camera apparatus 14. The control unit 153 may also perform control and processing relating to capturing of a moving image performed by the camera apparatus 14, with reference to the table in which the direction and the imaging magnification of the camera apparatus 14 are determined in accordance with the imaging location.

The moving image managing unit 155 stores and manages a camera moving image obtained from the camera apparatus 14 and information obtained from the radiation imaging control apparatus 13 in relation to (in association with) each other.

The display unit 156 is constituted by, for example, a liquid crystal display, and displays a camera moving image managed by the moving image managing unit 155, a camera imaging setting screen, and so on.

The operation unit 157 is constituted by, for example, a mouse and keyboard and various buttons, and accepts input information from the operator.

The communication unit 158 performs communication with the radiation imaging control apparatus 13 and the camera apparatus 14 and performs reception of imaging instruction information from the radiation imaging control apparatus 13, for example.

Figure 6:
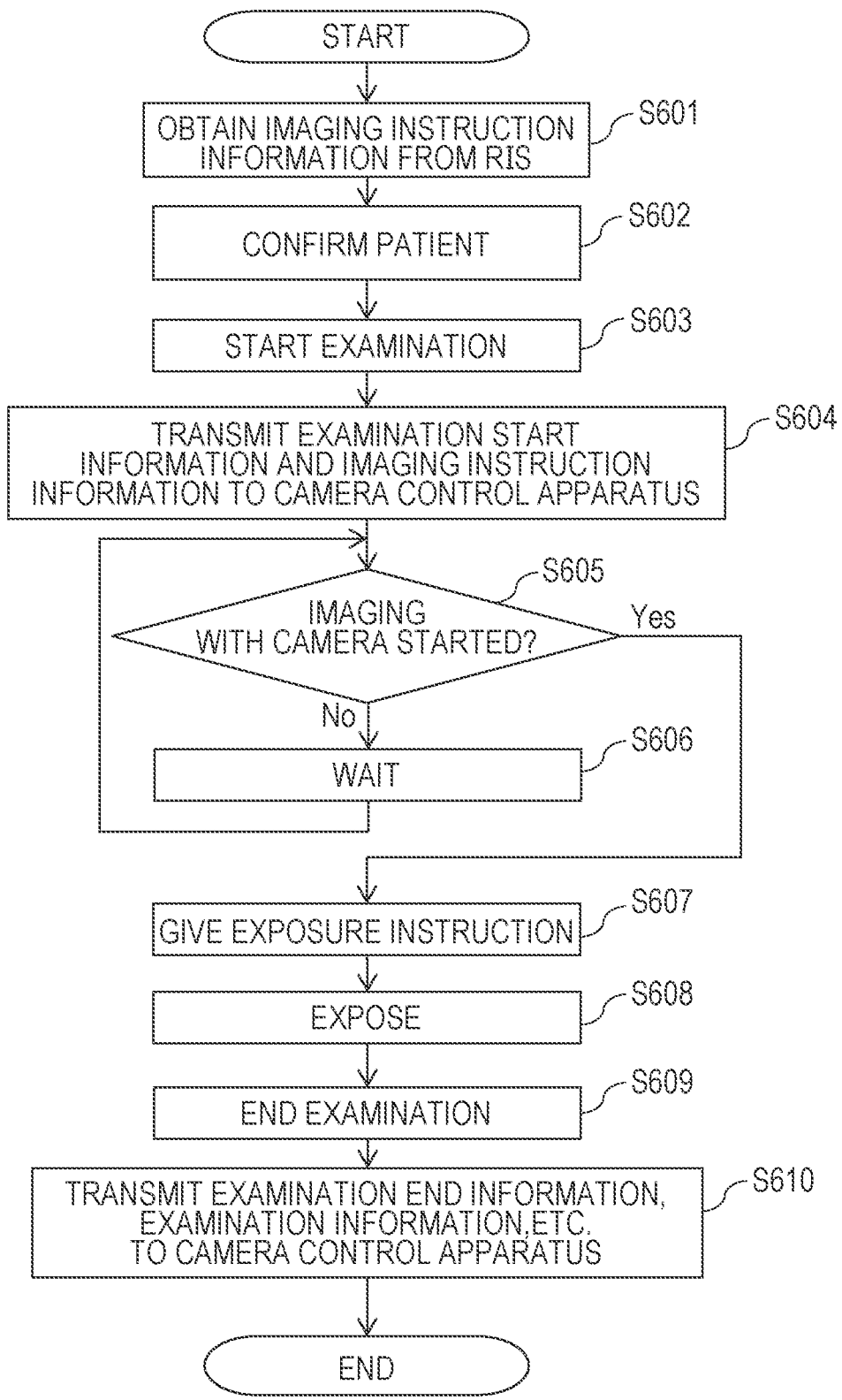
FIG. 6 illustrates the first embodiment of the present invention and is a flowchart illustrating an example of a processing procedure of a control method performed by the radiation imaging control apparatus illustrated in FIG. 1.

FIG. 6 illustrates the first embodiment of the present invention and is a flowchart illustrating an example of a processing procedure of a control method performed by the radiation imaging control apparatus 13 illustrated in FIG. 1.

When a radiographer operates the operation unit 132 of the radiation imaging control apparatus 13 to input an instruction to obtain examination information (including imaging instruction information) from the external system 20, the external system cooperating unit 134 obtains the examination information from the external system 20 in step S601. Although the configuration of obtaining the examination information from the external system 20 is described in the present embodiment, a configuration in which a radiographer manually inputs the examination information via the operation unit 132 may be used, for example.

Subsequently, in step S602, the radiographer confirms information (such as the patient ID and the patient name) regarding a patient who has come to the imaging room and guides the patient to the imaging location in the imaging room.

Thereafter, the radiographer gives an examination start instruction for an examination of the patient via the operation unit 132. Subsequently, in step S603, for example, the control unit 133 detects this.

Subsequently, in response to the examination start instruction from the radiographer, the control unit 133 transmits information indicating that the examination has been started (circumstances in which the examination is performed) and the imaging instruction information of the corresponding examination to the camera control apparatus 15 in step S604.

Subsequently, in step S605, the control unit 133 performs communication with the camera control apparatus 15 and determines whether capturing of a camera moving image has been started by the camera apparatus 14.

If capturing of the camera moving image has not been started yet by the camera apparatus 14 as a result of the determination in step S605 (S605/No), the process proceeds to step S606.

After the process proceeds to step S606, the control unit 133 waits for a predetermined time. The process then returns to step S605.

On the other hand, if capturing of the camera moving image has been started by the camera apparatus 14 as a result of the determination in step S605 (S605/Yes), the process proceeds to step S607.

After the process proceeds to step S607, the control unit 133 instructs the radiation generating apparatus 11 to expose the patient to radiation in response to the start of camera imaging by the radiographer.

The radiation generating apparatus 11 that has received the radiation exposure instruction from the control unit 133 in step S607 exposes the patient serving as an object to radiation in step S608. Thereafter, the radiation detecting apparatus 12 detects, as an image signal (radiation image signal), radiation that is emitted from the radiation generating apparatus 11 and that is incident thereto, generates a radiation imaging image based on this radiation image signal, and outputs the generated radiation imaging image to the radiation imaging control apparatus 13.

Subsequently, in step S609, the control unit 133 obtains the radiation imaging image output from the radiation imaging control apparatus 13 and displays the radiation imaging image on the display unit 131. Then, the radiographer checks the radiation imaging image displayed on the display unit 131, and inputs an examination end instruction via the operation unit 132. The control unit 133 then detects this.

Subsequently, in step S610, the control unit 133 transmits information indicating that the examination has been ended (circumstances in which the examination is performed), the examination information, and the radiation imaging image to the camera control apparatus 15.

After the processing of step S610 ends, the process of the flowchart illustrated in FIG. 6 ends.

Figure 7:
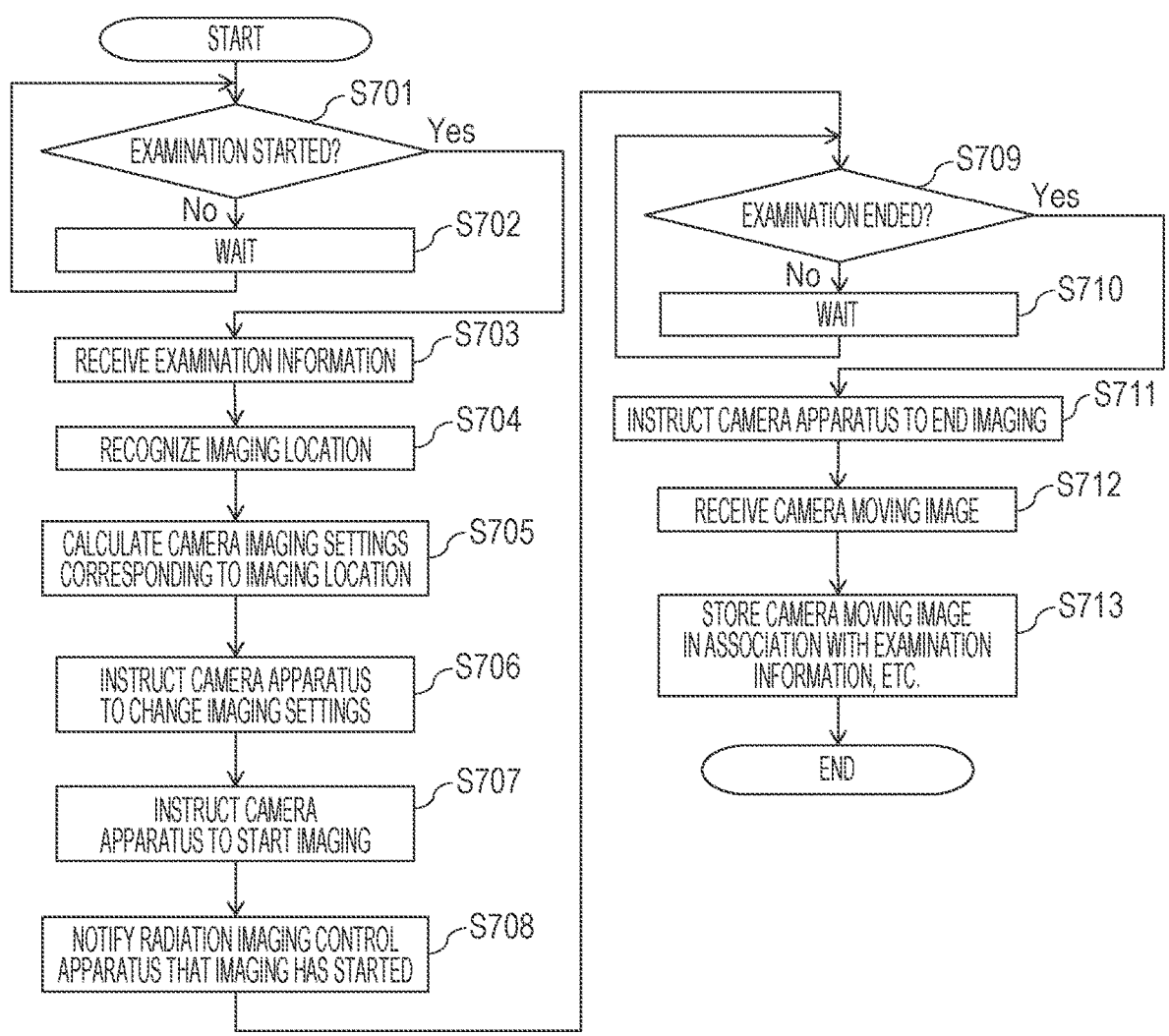
FIG. 7 illustrates the first embodiment of the present invention and is a flowchart illustrating an example of a processing procedure of a control method performed by the camera control apparatus illustrated in FIG. 1.

FIG. 7 illustrates the first embodiment of the present invention and is a flowchart illustrating an example of a processing procedure of a control method performed by the camera control apparatus 15 illustrated in FIG. 1.

First, in step S701, the control unit 153 determines whether an examination start notification has been received from the radiation imaging control apparatus 13.

If the examination start notification has not been received from the radiation imaging control apparatus 13 yet as a result of the determination in step S701 (S701/No), the process proceeds to step S702.

After the process proceeds to step S702, the control unit 153 waits for a predetermined time. The process then returns to step S701.

On the other hand, if the examination start notification has been received from the radiation imaging control apparatus 13 as a result of the determination in step S701 (S701/Yes), the process proceeds to step S703.

After the process proceeds to step S703, the communication unit 158 receives, after the start of examination, examination information (including imaging instruction information) of the corresponding examination from the radiation imaging control apparatus 13.

Subsequently, in step S704, the imaging location recognizing unit 151 recognizes the imaging location at which radiation imaging is performed in an imaging room on the basis of the imaging instruction information included in the examination information received in step S703.

Subsequently, in step S705, the imaging setting calculating unit 152 calculates settings of the camera apparatus 14 (for example, imaging settings such as the direction (orientation) and the imaging magnification of the camera apparatus 14) in accordance with the imaging location recognized in step S704. Note that when the imaging magnification is calculated, for example, the magnification with which the imaging location recognized in step S704 becomes the sharpest may be selected, the magnification with which the entire radiation detecting apparatus 12 is included in the imaging range may be selected, or the magnification with which the patient's face is included in the imaging range may be selected.

Subsequently, in step S706, the control unit 153 instructs the camera apparatus 14 to change the settings of the camera apparatus 14 to the settings (imaging settings) calculated in step S705.

Subsequently, in step S707, the control unit 153 instructs the camera apparatus 14 to start imaging.

Subsequently, in step S708, the control unit 153 notifies the radiation imaging control apparatus 13 that the camera apparatus 14 has started imaging.

Subsequently, in step S709, the control unit 153 performs communication with the radiation imaging control apparatus 13 to determine whether an examination end notification has been received from the radiation imaging control apparatus 13.

If the examination end notification has not been received from the radiation imaging control apparatus 13 yet as a result of the determination in step S709 (S709/No), the process proceeds to step S710.

After the process proceeds to step S710, the control unit 153 waits for a predetermined time. The process then returns to step S709.

On the other hand, if the examination end notification has been received from the radiation imaging control apparatus 13 as a result of the determination in step S709 (S709/Yes), the process proceeds to step S711.

After the process proceeds to step S711, the control unit 153 instructs the camera apparatus 14 to end imaging in response to the end of the examination.

Subsequently, in step S712, the moving image managing unit 155 receives a camera moving image captured by the camera apparatus 14 from the camera apparatus 14.

Subsequently, in step S713, the moving image managing unit 155 stores, as camera moving image management information, the camera moving image received in step S712 and the examination information (including the imaging instruction information) received in step S703 in association with each other. At this time, the moving image managing unit 155 may obtain the radiation imaging image from the radiation imaging control apparatus 13, and may further store, as the camera moving image management information, the obtained radiation imaging image in association with the camera moving image and the examination information that are described above.

After the processing of step S713 ends, the process of the flowchart illustrated in FIG. 7 ends.

Figure 8:
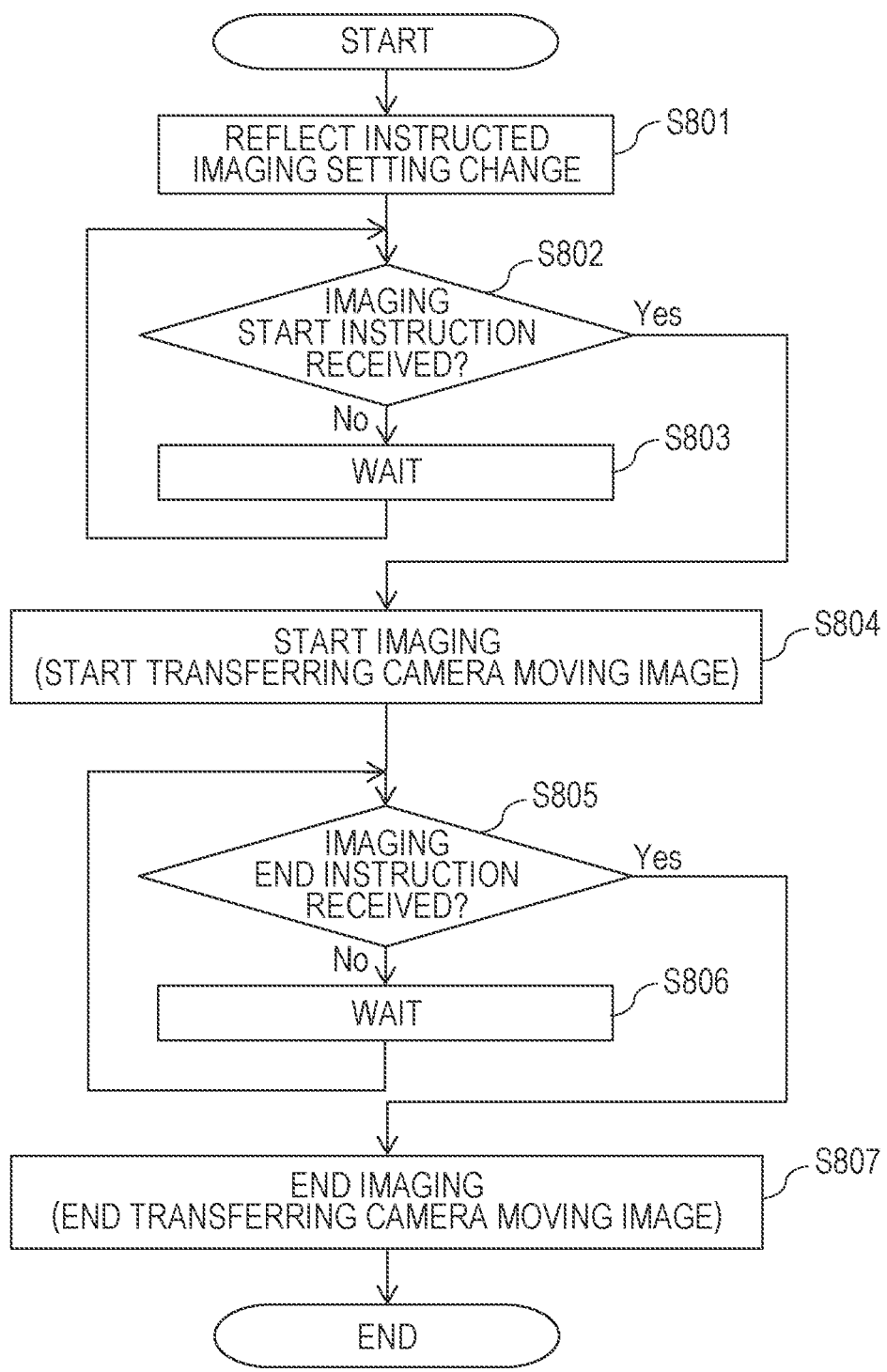
FIG. 8 illustrates the first embodiment of the present invention and is a flowchart illustrating an example of a processing procedure of a control method performed by the camera apparatus illustrated in FIG. 1.

FIG. 8 illustrates the first embodiment of the present invention and is a flowchart illustrating an example of a processing procedure of a control method performed by the camera apparatus 14 illustrated in FIG. 1.

First, in step S801, the camera apparatus 14 reflects in the imaging unit 141 the settings of the camera apparatus 14 to which the camera control apparatus 15 has instructed the camera apparatus 14 to change (in S706).

Subsequently, in step S802, the camera apparatus 14 determines whether an imaging start instruction has been received from the camera control apparatus 15.

If the imaging start instruction has not been received from the camera control apparatus 15 yet as a result of the determination in step S802 (S802/No), the process proceeds to step S803.

After the process proceeds to step S803, the camera apparatus 14 waits for a predetermined time. The process then returns to step S802.

On the other hand, if the imaging start instruction has been received from the camera control apparatus 15 as a result of the determination in step S802 (S802/Yes), the process proceeds to step S804.

After the process proceeds to step S804, the imaging unit 141 starts camera imaging in response to the imaging start instruction, and starts storing a camera moving image in the storage unit 143. At the same time with the start of camera imaging by the imaging unit 141, the communication unit 142 starts transferring the camera moving image that is being captured to the camera control apparatus 15 in real time.

Subsequently, in step S805, the camera apparatus 14 determines whether an imaging end instruction has been received from the camera control apparatus 15.

If the imaging end instruction has not been received from the camera control apparatus 15 yet as a result of the determination in step S805 (S805/No), the process proceeds to step S806.

After the process proceeds to step S806, the camera apparatus 14 waits for a predetermined time. The process then returns to step S805.

On the other hand, if the imaging end instruction has been received from the camera control apparatus 15 as a result of the determination in step S805 (S805/Yes), the process proceeds to step S807.

After the process proceeds to step S807, the imaging unit 141 ends camera imaging in response to the imaging end instruction, and ends storing of the camera moving image in the storage unit 143. In addition, after the end of camera imaging, the communication unit 142 ends real-time transfer of the camera moving image to the camera control apparatus 15.

After the processing of step S807 ends, the process of the flowchart illustrated in FIG. 8 ends.

A detailed processing procedure of imaging location recognition processing performed in step S704 of FIG. 7 will be described next.

Figure 9:
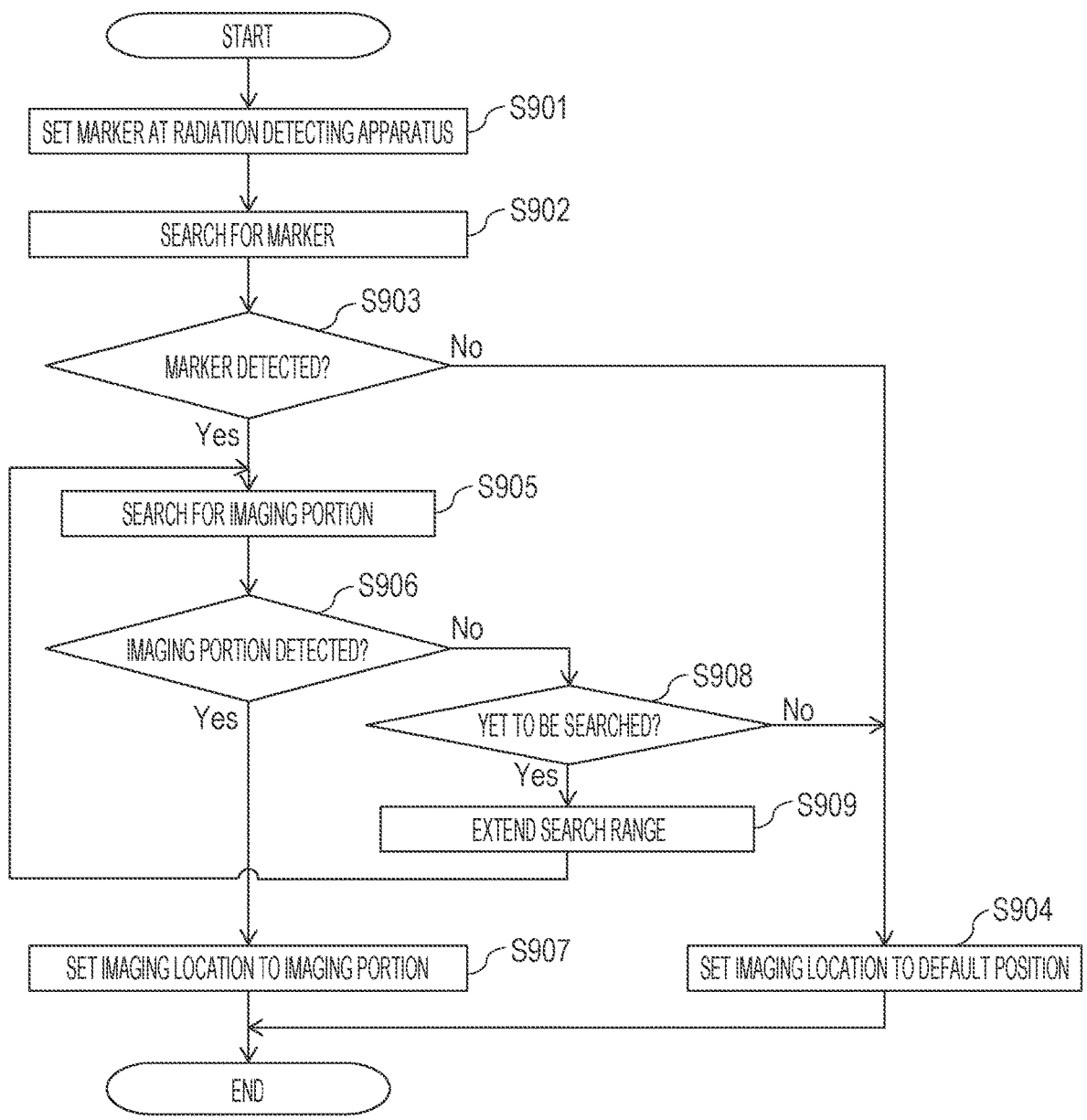
FIG. 9 illustrates the first embodiment of the present invention and is a flowchart illustrating an example of a detailed processing procedure of imaging location recognition processing performed in step S704 of FIG. 7.

FIG. 9 illustrates the first embodiment of the present invention and is a flowchart illustrating an example of a detailed processing procedure of the imaging location recognition processing performed in step S704 of FIG. 7.

First, in step S901, a radiographer sets a detection marker at the radiation detecting apparatus 12 in advance before imaging by the camera apparatus 14 is performed.

Subsequently, in step S902, the imaging location recognizing unit 151 performs processing of searching for the marker set at the radiation detecting apparatus 12 from a camera moving image transmitted from the camera apparatus 14 in real time. At this time, the imaging location recognizing unit 151 may adopt a configuration of searching for the marker using any publicly known image recognition technique.

Subsequently, in step S903, the imaging location recognizing unit 151 determines whether the marker is successfully detected as a result of the search performed in step S902.

If the detection of the marker is not successful as a result of the determination in step S903 (S903/No), the process proceeds to step S904.

After the process proceeds to step S904, the imaging location recognizing unit 151 performs recognition for setting the imaging location to a default position set by the radiographer in advance. Note that the default position set at this time may be any position.

On the other hand, if the detection of the marker is successful as a result of the determination in step S903 (S903/Yes), the process proceeds to step S905.

After the process proceeds to step S905, the imaging location recognizing unit 151 performs image processing on a range around the marker detected in step S902 among the camera moving image transmitted from the camera apparatus 14 to search for an imaging portion of an object included in the examination information received in step S703.

Subsequently, in step S906, the imaging location recognizing unit 151 determines whether the imaging portion is successfully detected as a result of the search performed in step S905.

If the detection of the imaging portion is successful as a result of the determination in step S906 (S906/Yes), the process proceeds to step S907.

After the process proceeds to step S907, the imaging location recognizing unit 151 performs recognition for setting the imaging location to the position of the imaging portion detected in step S905.

On the other hand, if the detection of the imaging portion is not successful as a result of the determination in step S906 (S906/No), the process proceeds to step S908.

After the process proceeds to step S908, the imaging location recognizing unit 151 determines whether there is a range yet to be searched. if there is no range yet to be searched as a result of this determination (S908/No), the process proceeds to step S904, and the recognition for setting the imaging location to the default position is performed as described above.

In addition, if there is a range yet to be searched as a result of the determination in step S908 (S908/Yes), the process proceeds to step S909.

After the process proceeds to step S909, the imaging location recognizing unit 151 performs a setting for extending the search range in which the search is to be performed in step S905. Thereafter, the process returns to step S905, and the processing of step S905 and the subsequent steps is performed in the search range set in step S909.

If the processing of step S904 ends, or if the processing of step S907 ends, the process of the flowchart illustrated in FIG. 9 ends.

Note that in the above-described processing of the flowchart illustrated in FIG. 9, the configuration has been described in which the detection marker is set at the radiation detecting apparatus 12 in step S901 and the radiation detecting apparatus 12 is detected by detecting the marker in the subsequent processing. However, the present invention is not limited to this configuration, and a configuration in which the radiation detecting apparatus 12 is directly detected from the camera moving image transmitted from the camera apparatus 14 without attaching the marker to the radiation detecting apparatus 12 may also be used in the present invention.

In addition, in the search processing performed in step S905 of FIG. 9, the start position of the search for the imaging location and the search range may be determined using the examination information received in step S703. For example, a correspondence table of the imaging portion and the imaging location may be prepared in advance, and the search may be started from a region around the default position of the imaging location in accordance with the received imaging portion.

An example of camera moving image management information managed by the moving image managing unit 155 will be described next.

FIG. 10 illustrates the first embodiment of the present invention and is a schematic diagram illustrating an example of camera moving image management information 1000 managed by the moving image managing unit 155 of the camera control apparatus 15 illustrated in FIG. 5. The camera moving image management information 1000 illustrated in FIG. 10 is a schematic diagram illustrating an example of camera moving image management information of a certain date (Oct. 13, 2017).

The camera moving image management information 1000 illustrated in FIG. 10 includes camera ID information 1010, camera moving image imaging date information 1020, and camera moving image management table information 1030. In addition, in the camera moving image management table information 1030, camera moving image ID information 1031, camera moving image imaging start time information 1032, camera moving image imaging end time information 1033, patient ID information 1034, patient name information 1035, examination ID information 1036, imaging portion information 1037, and radiation imaging image ID information 1038 are stored in association with one another.

The camera ID information 1010 is used for displaying a camera ID that enables information regarding the camera apparatus 14 such as the model name of the camera apparatus 14, the manufacturer name, and the installed location of the camera apparatus 14 to be uniquely identified.

The camera moving image ID information 1031 is used for displaying a camera moving image ID that enables camera moving image information such as the stored camera moving image, the imaging start time, and the imaging end time to be uniquely identified.

In addition, the examination information described above includes information on conditions of radiation imaging performed for each patient. For example, examples of the radiation imaging condition information include the imaging portion, the imaging direction, the radiation detecting apparatus 12 used in the examination, and the distance between the patient and the radiation generating apparatus 11. In FIG. 10, the examination information is displayed as the examination ID information 1036 that enables this examination information to be uniquely identified.

In addition, the radiation imaging image information is information regarding a radiation imaging image received from the radiation imaging control apparatus 13 and is, for example, a file path of the radiation imaging image. In FIG. 10, the radiation imaging image information is displayed as the radiation imaging image ID information 1038 that enables this radiation imaging image information to be uniquely identified.

The camera control apparatus 15 according to the first embodiment recognizes the imaging location at which radiation imaging is performed in the imaging room (S704, FIG. 9) and calculates the settings of the camera apparatus 14 in accordance with the recognized imaging location (S705).

Such a configuration enables the camera apparatus 14 to record an appropriate video image relating to circumstances in which radiation imaging is performed in an imaging room.

Further, the camera control apparatus 15 according to the first embodiment calculates the direction and the imaging magnification of the camera apparatus 14 as the settings of the camera apparatus 14 according to the imaging location (S705).

Such a configuration enables a video image relating to circumstances in which radiation imaging is performed in an imaging room to be recorded with the appropriate direction of the camera apparatus 14 at a high image resolution.

Second Embodiment

A second embodiment of the present invention will be described next. Note that description of features that are common to the first embodiment described above is omitted and features different from those of the first embodiment described above will be described in the second embodiment described below.

Specifically, the second embodiment differs from the first embodiment in a detailed processing procedure of the imaging location recognition processing performed in step S704 of FIG. 7.

Figure 11:
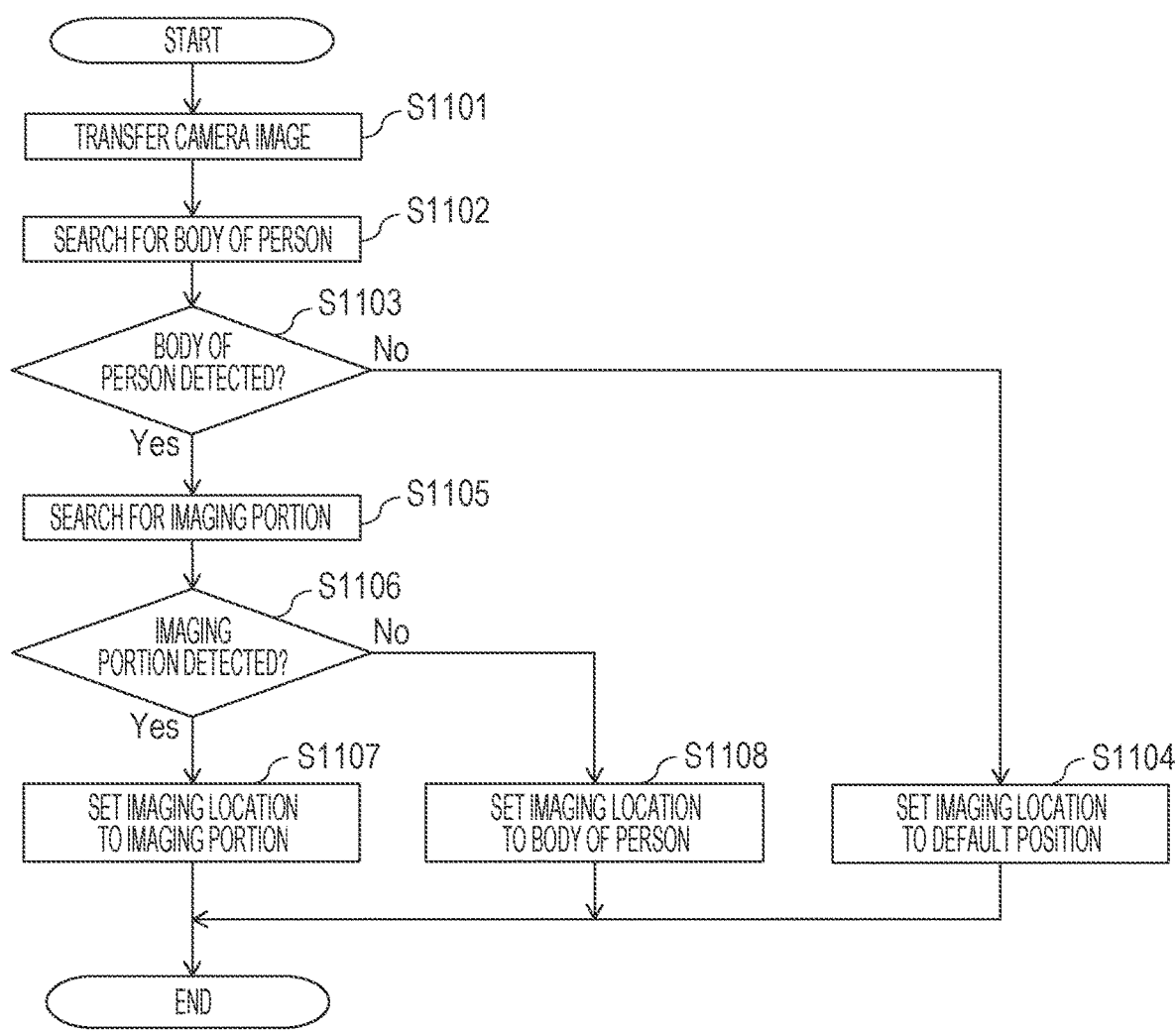
FIG. 11 illustrates a second embodiment of the present invention and is a flowchart illustrating an example of a detailed processing procedure of imaging location recognition processing performed in step S704 of FIG. 7.

FIG. 11 illustrates the second embodiment of the present invention and is a flowchart illustrating an example of a detailed processing procedure of the imaging location recognition processing performed in step S704 of FIG. 7.

First, in step S1101, the imaging location recognizing unit 151 receives a camera moving image transmitted from the camera apparatus 14 in real time.

Subsequently, in step S1102, the imaging location recognizing unit 151 performs processing of searching for a body of a patient serving as an object from the camera moving image received in step S1101. At this time, the imaging location recognizing unit 151 may adopt a configuration of searching for the body of a person using any publicly known image recognition technique.

Subsequently, in step S1103, the imaging location recognizing unit 151 determines whether the body of a person is successfully detected as a result of the search performed in step S1102.

If the detection of the body of a person is not successful as a result of the determination in step S1103 (S1103/No), the process proceeds to step S1104.

After the process proceeds to step S1104, the imaging location recognizing unit 151 performs recognition for setting the imaging location to a default position set by the radiographer in advance. Note that the default position set at this time may be any position.

On the other hand, if the detection of the body of a person is successful as a result of the determination in step S1103 (S1103/Yes), the process proceeds to step S1105.

After the process proceeds to step S1105, the imaging location recognizing unit 151 performs image processing on a range around the body of a person detected in step S1102 among the camera moving image transmitted from the camera apparatus 14 to search for an imaging portion of the object included in the examination information received in step S703.

Subsequently, in step S1106, the imaging location recognizing unit 151 determines whether the imaging portion is successfully detected as a result of the search performed in step S1105.

If the detection of the imaging portion is successful as a result of the determination in step S1106 (S1106/Yes), the process proceeds to step S1107.

After the process proceeds to step S1107, the imaging location recognizing unit 151 performs recognition for setting the imaging location to the position of the imaging portion detected in step S1105.

On the other hand, if the detection of the imaging portion is not successful as a result of the determination in step S1106 (S1106/No), the process proceeds to step S1108.

After the process proceeds to step S1108, the imaging location recognizing unit 151 performs recognition for setting the imaging location to the position of the body of a person detected in step S1102.

Then, if the processing of step S1104 ends, if the processing of step S1107 ends, or if the processing of step S1108 ends, the process of the flowchart illustrated in FIG. 11 ends.

Note that in the above-described processing of the flowchart illustrated in FIG. 11, the configuration has been described in which a search for detecting the body of a person is performed using a camera image in step S1102. However, the present invention is not limited to this configuration. For example, a configuration may be used in which an infrared sensor is installed near the camera apparatus 14, a far-infrared image that records the circumstance in the imaging room is transmitted to the imaging location recognizing unit 151 from this infrared sensor, and the imaging location recognizing unit 151 performs a search for detecting the body of a person using this far-infrared image.

As in the first embodiment described above, the camera control apparatus 15 according to the second embodiment enables the camera apparatus 14 to record an appropriate video image relating to circumstances in which radiation imaging is performed in an imaging room. Further, in the second embodiment, the imaging location is successfully recognized even if the camera control apparatus 15 fails to detect the radiation detecting apparatus 12 as a result of the object covering the radiation detecting apparatus 12 due to the arrangement of the object, the radiation generating apparatus 11, the radiation detecting apparatus 12, and the camera apparatus 14.

Third Embodiment

A third embodiment of the present invention will be described next. Note that description of features that are common to the first and second embodiments described above is omitted and features different from those of the first and second embodiments described above will be described in the third embodiment described below.

In the third embodiment, a configuration will be described which assumes that a radiographer browses a camera moving image associated with a radiation imaging image.

Figure 12:
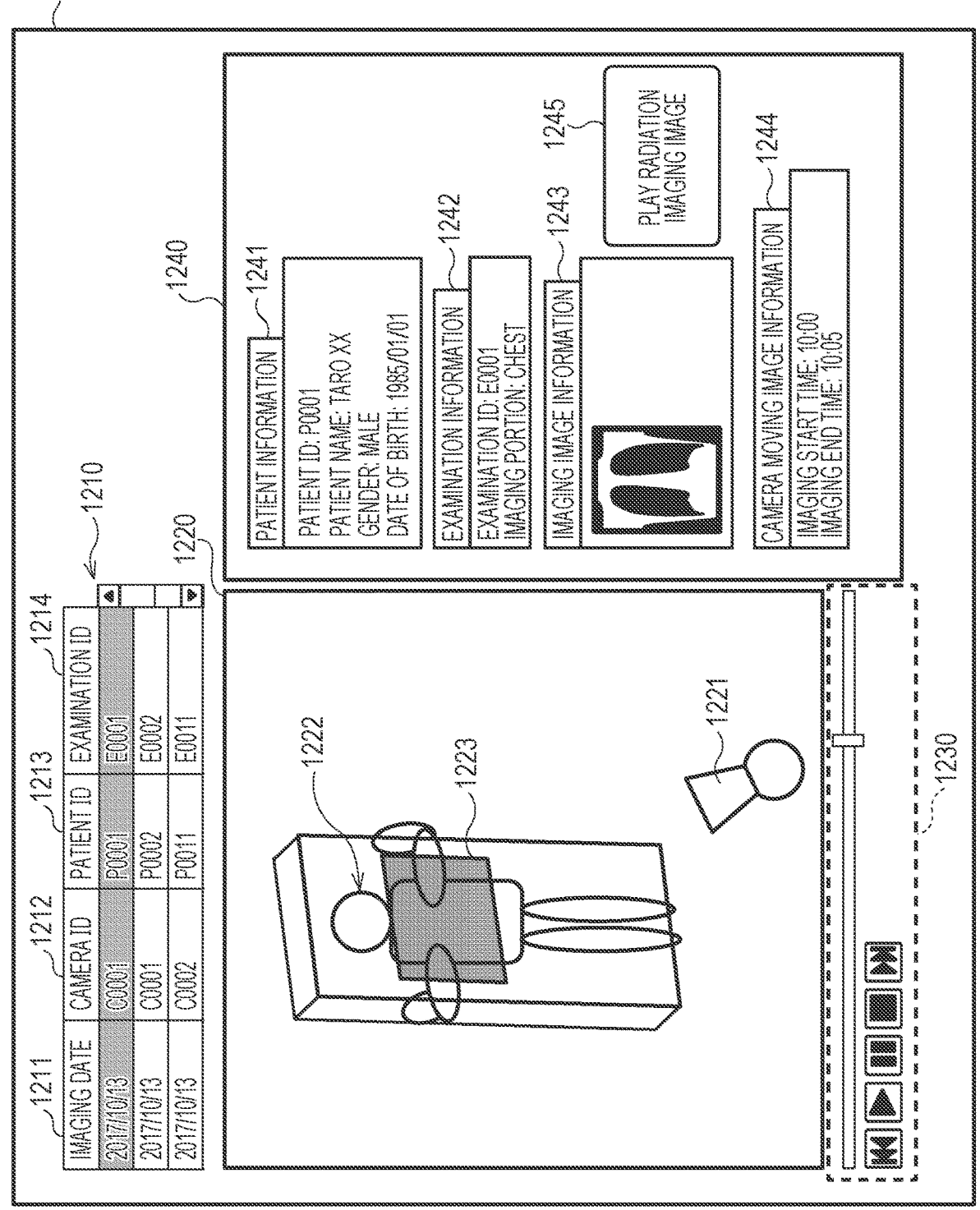
FIG. 12 illustrates a third embodiment of the present invention and is a schematic diagram illustrating an example of a GUI display screen in which a radiation imaging image is associated with a camera moving image.

FIG. 12 illustrates the third embodiment of the present invention and is a schematic diagram illustrating an example of a GUI display screen 1200 in which a radiation imaging image is associated with a camera moving image. It is assumed in the present embodiment that this GUI display screen 1200 is displayed on the display unit 156 of the camera control apparatus 15. However, a configuration in which the GUI display screen 1200 is displayed on the display unit 131 of the radiation imaging control apparatus 13, for example, may also be used.

As illustrated in FIG. 12, the GUI display screen 1200 is provided with a camera moving image list display portion 1210, a camera moving image display portion 1220, a camera moving image control portion 1230, and a related information display portion 1240.

The camera moving image list display portion 1210 displays a list of camera moving images stored by the moving image managing unit 155 of the camera control apparatus 15. Specifically, the camera moving image list display portion 1210 displays a list of imaging date information 1211, camera ID information 1212, patient ID information 1213, and examination ID information 1214. A radiographer narrows down a camera moving image to be browsed based on the information displayed in the camera moving image list display portion 1210 to select the corresponding record.

The camera moving image display portion 1220 displays a camera moving image selected by the radiographer from the list displayed in the camera moving image list display portion 1210. Specifically, the camera moving image display portion 1220 illustrated in FIG. 12 displays a camera moving image including a radiation generating apparatus 1221 corresponding to the radiation generating apparatus 11, a radiation detecting apparatus 1223 corresponding to the radiation detecting apparatus 12, and an object 1222 corresponding to a patient located between the radiation generating apparatus 1221 and the radiation detecting apparatus 1223.

Via the camera moving image control portion 1230, control is performed on the camera moving image that is being displayed in the camera moving image display portion 1220. Examples of the control include play, pause, stop, rewind, forward, and full-screen display. However, in the present embodiment, the control is not limited to these. The radiographer performs these kinds of control on the camera moving image to browse the circumstances in which radiation imaging is performed.

The related information display portion 1240 displays information relating to the camera moving image selected by the radiographer from the list displayed in the camera moving image list display portion 1210. For example, the camera moving image management information (information regarding the camera apparatus 14, the camera moving image information, the patient information, the examination information, and the radiation imaging image information) illustrated in FIG. 10 is displayed. Specifically, in the example illustrated in FIG. 12, the related information display portion 1240 displays patient information 1241, examination information 1242, imaging image information 1243, camera moving image information 1244, and a radiation imaging image play button 1245. Note that as for the radiation imaging image, the radiation imaging image may be displayed in a full screen mode in response to clicking of the radiation imaging image play button 1245.

The camera control apparatus 15 according to the third embodiment also provides advantages similar to those of the camera control apparatus 15 according to the first embodiment described above.

Fourth Embodiment

A fourth embodiment of the present invention will be described next. Note that description of features that are common to the first to third embodiments described above is omitted and features different from those of the first to third embodiments described above will be described in the fourth embodiment described below.

Figure 13:
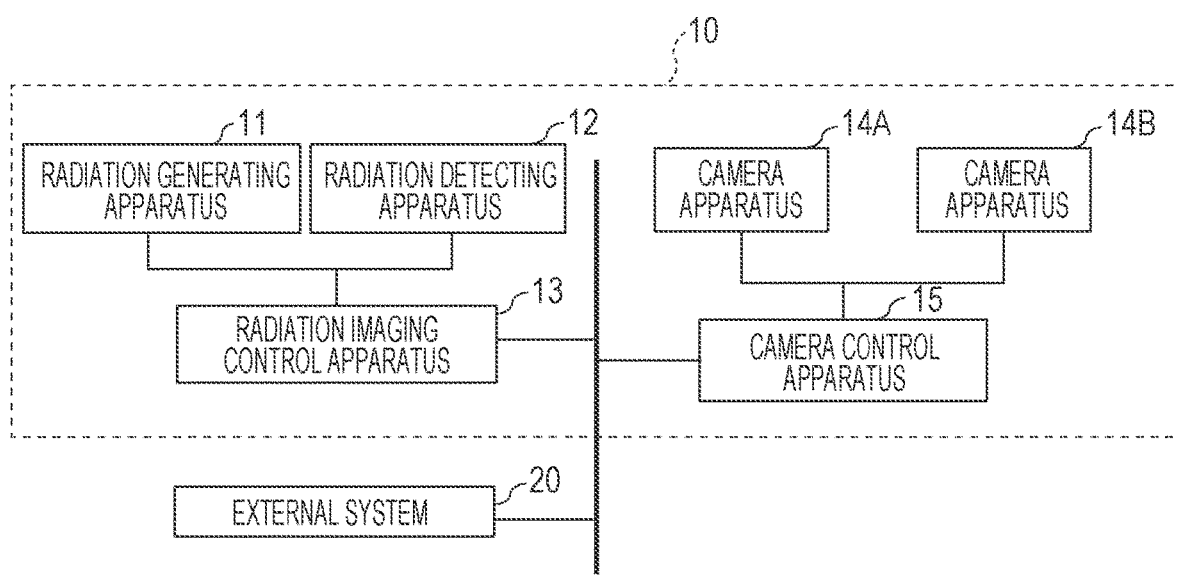
FIG. 13 is a schematic diagram illustrating an example of an overview of a configuration of a radiation imaging system according to a fourth embodiment of the present invention.

FIG. 13 is a schematic diagram illustrating an example of an overview of a configuration of the radiation imaging system 10 according to the fourth embodiment of the present invention. In FIG. 13, components similar to those illustrated in FIG. 1 are denoted by the same reference signs, and detailed description thereof is omitted.

As illustrated in FIG. 13, the radiation imaging system 10 according to the fourth embodiment includes the radiation generating apparatus 11, the radiation detecting apparatus 12, the radiation imaging control apparatus 13, a camera apparatus 14A, a camera apparatus 14B, and the camera control apparatus 15. In addition, as illustrated in FIG. 13, the radiation imaging system 10 according to the fourth embodiment is configured to be able to cooperate with the external system 20. Specifically, the radiation imaging system 10 according to the fourth embodiment illustrated in FIG. 13 is different from the radiation imaging system 10 according to the first embodiment illustrated in FIG. 1 in that the plurality of camera apparatuses 14A and 14B are included.

Each of the camera apparatus 14A and the camera apparatus 14B is an apparatus that records a video image relating to circumstances in which radiation imaging is performed. Specifically, in the present embodiment, each of the camera apparatus 14A and the camera apparatus 14B records a different moving image (camera moving image) as a video image relating to circumstances in which radiation imaging is performed in an imaging room and transfers this camera moving image to the camera control apparatus 15.

The camera control apparatus 15 is connected to the camera apparatus 14A and the camera apparatus 14B with a cable or wirelessly and controls operations of the camera apparatus 14A and the camera apparatus 14B.

Figure 14:
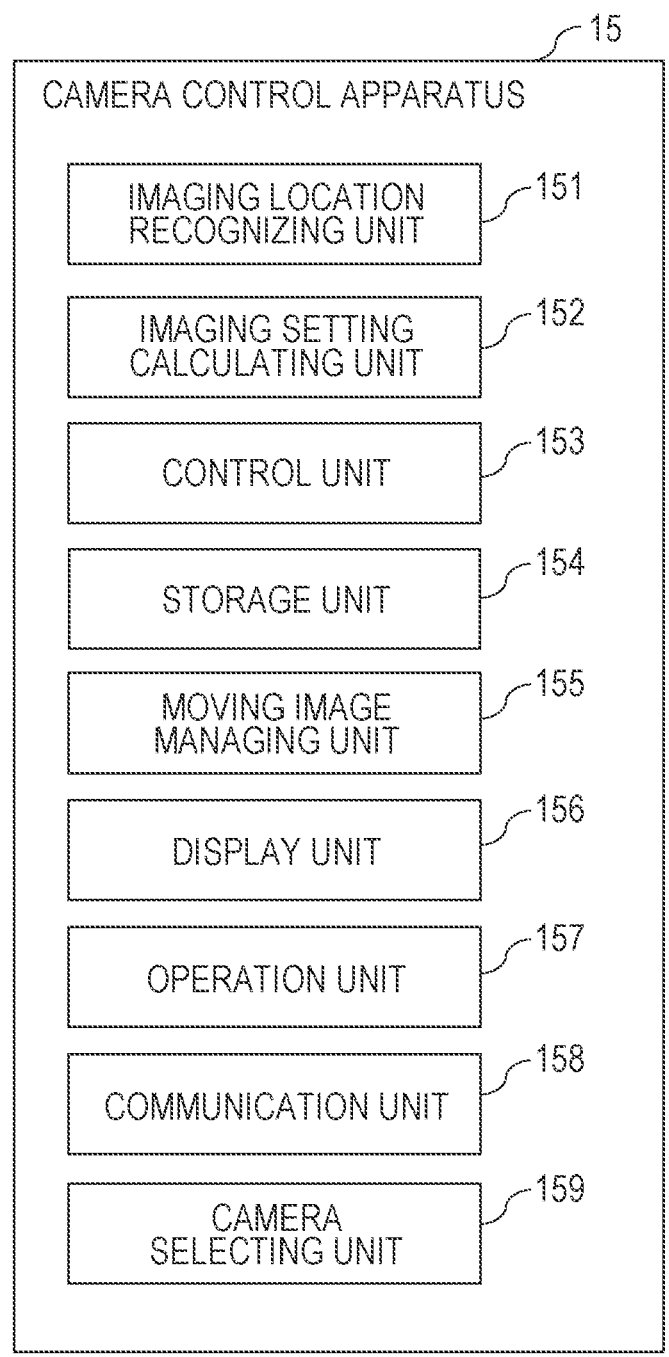
FIG. 14 illustrates the fourth embodiment of the present invention and is a schematic diagram illustrating an example of a functional configuration of a camera control apparatus illustrated in FIG. 13.

FIG. 14 illustrates the fourth embodiment of the present invention and is a schematic diagram illustrating an example of a functional configuration of the camera control apparatus 15 illustrated in FIG. 13. In FIG. 14, components similar to those illustrated in FIG. 5 are denoted by the same reference signs, and detailed description thereof is omitted.

As illustrated in FIG. 14, the camera control apparatus 15 according to the present embodiment includes the imaging location recognizing unit 151, the imaging setting calculating unit 152, the control unit 153, the storage unit 154, the moving image managing unit 155, the display unit 156, the operation unit 157, the communication unit 158, and a camera selecting unit 159. That is, the camera control apparatus 15 according to the fourth embodiment further includes the camera selecting unit 159 in addition to the individual constituent units of the camera control apparatus 15 according to the first embodiment illustrated in FIG. 5.

The camera selecting unit 159 selects one camera apparatus 14 from among the plurality of camera apparatuses 14A and 14B on the basis of imaging instruction information included in examination information that is transmitted and obtained from the radiation imaging control apparatus 13.

FIG. 15 illustrates the fourth embodiment of the present invention and is a diagram illustrating an example of a correspondence table used by the camera selecting unit 159 illustrated in FIG. 14 to select one camera apparatus 14. Specifically, FIG. 15 illustrates an example of a correspondence table of the imaging portion and the camera apparatus.

The present embodiment adopts a configuration in which the camera ID of the corresponding camera apparatus is managed for each imaging portion. It is assumed herein that the camera ID of the camera apparatus 14A illustrated in FIG. 13 is C0001 and the camera ID of the camera apparatus 14B illustrated in FIG. 13 is C0002. In this case, a configuration is adopted in which the camera selecting unit 159 selects the camera apparatus 14A if the chest is designated as the imaging portion in the imaging instruction information, and the camera selecting unit 159 selects the camera apparatus 14B if the hand is designated as the imaging portion in the imaging instruction information. In the present embodiment, the configuration of using the correspondence table of the imaging portion and the camera apparatus is described by way of example. However, the present invention is not limited to this configuration. For example, a configuration of using a correspondence table of the camera apparatus and the imaging table (for the standing position, the supine position, or the like) instead of the imaging portion may be used in the present invention.

Figure 16:
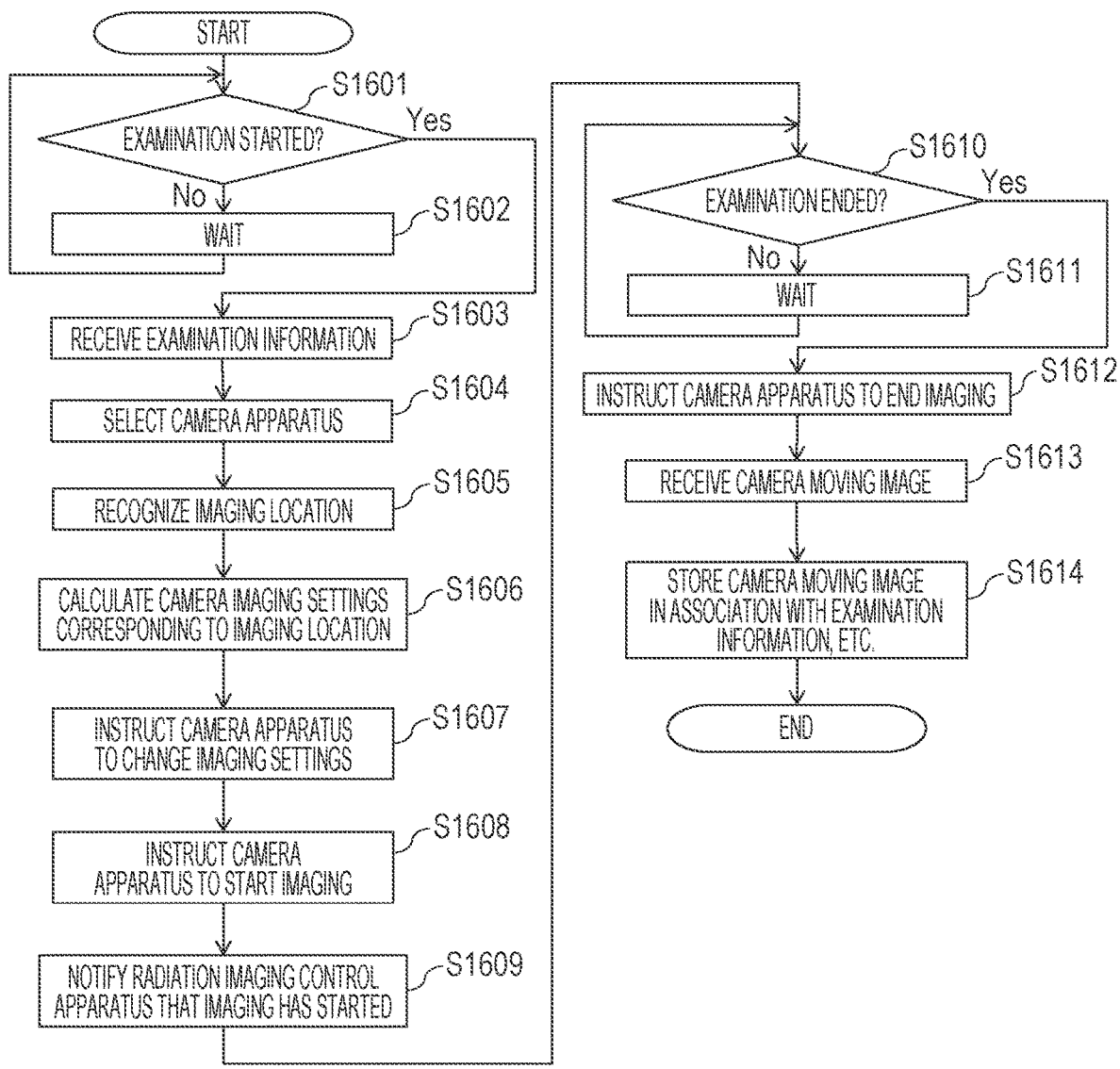
FIG. 16 illustrates the fourth embodiment of the present invention and is a flowchart illustrating an example of a processing procedure of a control method performed by the camera control apparatus illustrated in FIG. 13.

FIG. 16 illustrates the fourth embodiment of the present invention and is a flowchart illustrating an example of a processing procedure of a control method performed by the camera control apparatus 15 illustrated in FIG. 13.

First, in step S1601, the control unit 153 determines whether an examination start notification has been received from the radiation imaging control apparatus 13.

If the examination start notification has not been received from the radiation imaging control apparatus 13 yet as a result of the determination in step S1601 (S1601/No), the process proceeds to step S1602.

After the process proceeds to step S1602, the control unit 153 waits for a predetermined time. The process then returns to step S1601.

On the other hand, if the examination start notification has been received from the radiation imaging control apparatus 13 as a result of the determination in step S1601 (S1601/Yes), the process proceeds to step S1603.

After the process proceeds to step S1603, the communication unit 158 receives, after the start of examination, examination information (including imaging instruction information) of the corresponding examination from the radiation imaging control apparatus 13.

Subsequently, in step S1604, the camera selecting unit 159 selects one camera apparatus 14 from among the plurality of camera apparatuses 14A and 14B on the basis of the imaging instruction information included in the examination information received in step S1603. Specifically, the camera selecting unit 159 selects, using the correspondence table illustrated in FIG. 15, the camera apparatus 14A having the camera ID of C0001 if the chest is designated as the imaging portion in the imaging instruction information or the camera apparatus 14B having the camera ID of C0002 if the hand is designated as the imaging portion in the imaging instruction information.

Subsequently, in step S1605, the imaging location recognizing unit 151 recognizes the imaging location at which radiation imaging is performed in the imaging room on the basis of the imaging instruction information included in the examination information received in step S1603. The processing of the flowchart illustrated in FIG. 9 or the processing of the flowchart illustrated in FIG. 11 may be used as the detailed processing of this imaging location recognition processing performed in step S1605.

Subsequently, in step S1606, the imaging setting calculating unit 152 calculates settings of the camera apparatus 14 (for example, imaging settings such as the direction (orientation) and the imaging magnification of the camera apparatus 14) selected in step S1604, in accordance with the imaging location recognized in step S1605. Note that when the imaging magnification is calculated, for example, the magnification with which the imaging location recognized in step S1605 becomes the sharpest may be selected, the magnification with which the entire radiation detecting apparatus 12 is included in the imaging range may be selected, or the magnification with which the patient's face is included in the imaging range may be selected.

Subsequently, in step S1607, the control unit 153 instructs the camera apparatus 14 selected in step S1604 to change the settings of the camera apparatus 14 to the settings (imaging settings) calculated in step S1606.

Subsequently, in step S1608, the control unit 153 instructs the camera apparatus 14 selected in step S1604 to start imaging.

Subsequently, in step S1609, the control unit 153 notifies the radiation imaging control apparatus 13 that the camera apparatus 14 selected in step S1604 has started imaging.

Subsequently, in step S1610, the control unit 153 performs communication with the radiation imaging control apparatus 13 to determine whether an examination end notification has been received from the radiation imaging control apparatus 13.

If the examination end notification has not been received from the radiation imaging control apparatus 13 yet as a result of the determination in step S1610 (S1610/No), the process proceeds to step S1611.

After the process proceeds to step S1611, the control unit 153 waits for a predetermined time. The process then returns to step S1610.

On the other hand, if the examination end notification has been received from the radiation imaging control apparatus 13 as a result of the determination in step S1610 (S1610/Yes), the process proceeds to step S1612.

After the process proceeds to step S1612, the control unit 153 instructs the camera apparatus 14 selected in step S1604 to end imaging in response to the end of the examination.

Subsequently, in step S1613, the moving image managing unit 155 receives a camera moving image captured by the camera apparatus 14 from the camera apparatus 14 selected in step S1604.

Subsequently, in step S1614, the moving image managing unit 155 stores, as camera moving image management information, the camera moving image received in step S1613 and the examination information (including the imaging instruction information) received in step S1603 in association with each other. At this time, the moving image managing unit 155 may obtain the radiation imaging image from the radiation imaging control apparatus 13, and may further store, as the camera moving image management information, the obtained radiation imaging image in association with the camera moving image and the examination information that are described above.

After the processing of step S1614 ends, the process of the flowchart illustrated in FIG. 16 ends.

The camera control apparatus 15 according to the fourth embodiment selects one camera apparatus 14 from among the plurality of camera apparatuses 14A and 14B on the basis of imaging instruction information included in examination information received from the radiation imaging control apparatus 13 (S1604). Then, the camera control apparatus 15 according to the fourth embodiment recognizes the imaging location at which radiation imaging is performed in the imaging room (S1605), and calculates the settings of the camera apparatus 14 in accordance with the recognized imaging location (S1606).

Such a configuration enables the camera apparatus 14 to record an appropriate video image relating to circumstances in which radiation imaging is performed in an imaging room. Further, since one camera apparatus 14 is selected from among the plurality of camera apparatuses 14A and 14B on the basis of the imaging instruction information, a more appropriate video image relating to the circumstances in which radiation imaging is performed in the imaging room is successfully recorded.

Fifth Embodiment

A fifth embodiment of the present invention will be described next. Note that description of features that are common to the first to fourth embodiments described above is omitted and features different from those of the first to fourth embodiments described above will be described in the fifth embodiment described below.

In the fifth embodiment, a configuration will be described in which body movement of a patient serving as an object, which may become a cause of a failed image in radiation imaging, is detected and this body movement detection information is automatically added to examination information held by the radiation imaging system 10.

Figure 17:
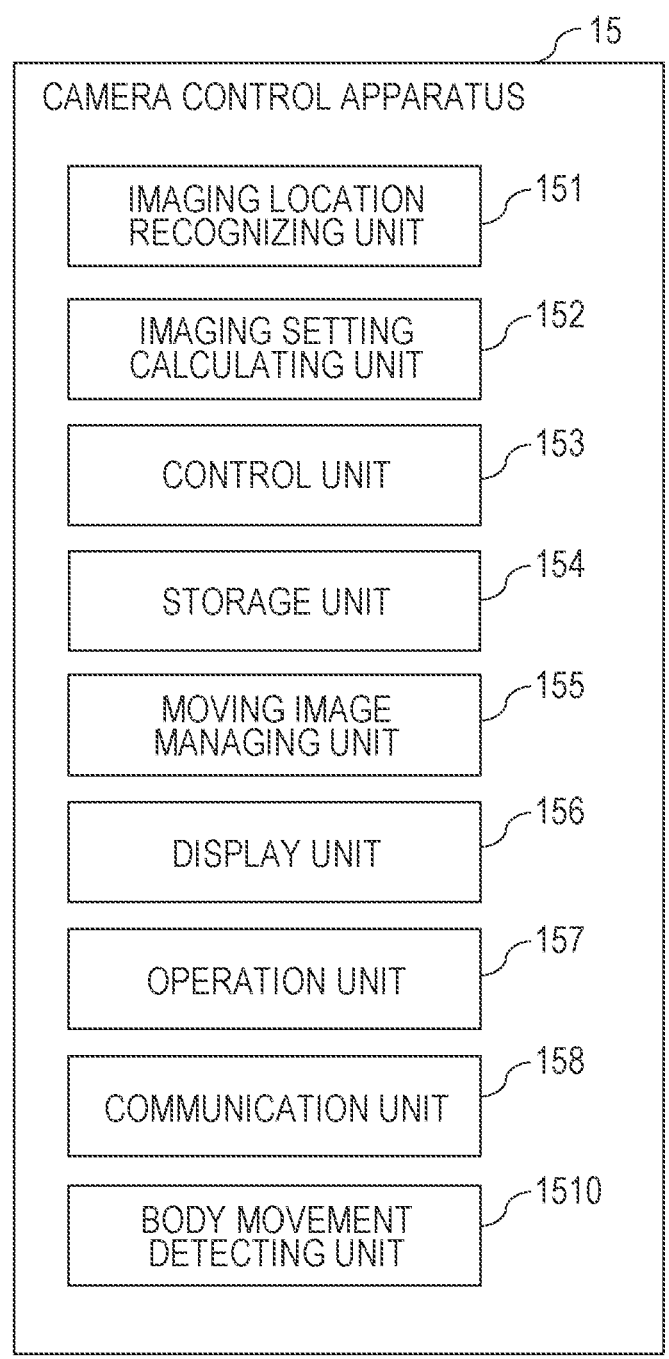
FIG. 17 illustrates a fifth embodiment of the present invention and is a schematic diagram illustrating an example of a functional configuration of the camera control apparatus illustrated in FIG. 1.

FIG. 17 illustrates the fifth embodiment of the present invention and is a schematic diagram illustrating an example of a functional configuration of the camera control apparatus 15 illustrated in FIG. 1. In FIG. 17, components similar to those illustrated in FIG. 5 are denoted by the same reference signs, and detailed description thereof is omitted.

As illustrated in FIG. 17, the camera control apparatus 15 according to the present embodiment includes the imaging location recognizing unit 151, the imaging setting calculating unit 152, the control unit 153, the storage unit 154, the moving image managing unit 155, the display unit 156, the operation unit 157, the communication unit 158, and a body movement detecting unit 1510. That is, the camera control apparatus 15 according to the fifth embodiment further includes the body movement detecting unit 1510 in addition to the individual constituent units of the camera control apparatus 15 according to the first embodiment illustrated in FIG. 5.

The body movement detecting unit 1510 detects body movement of a patient serving as an object from a camera moving image which is a video image relating to circumstances in which radiation imaging is performed in an imaging room and is obtained by the camera apparatus 14.

In the case of the present embodiment, a configuration is adopted in which the communication unit 158 transmits the body movement detection information to the radiation imaging control apparatus 13 if body movement of the patient is detected by the body movement detecting unit 1510.

Figure 18:
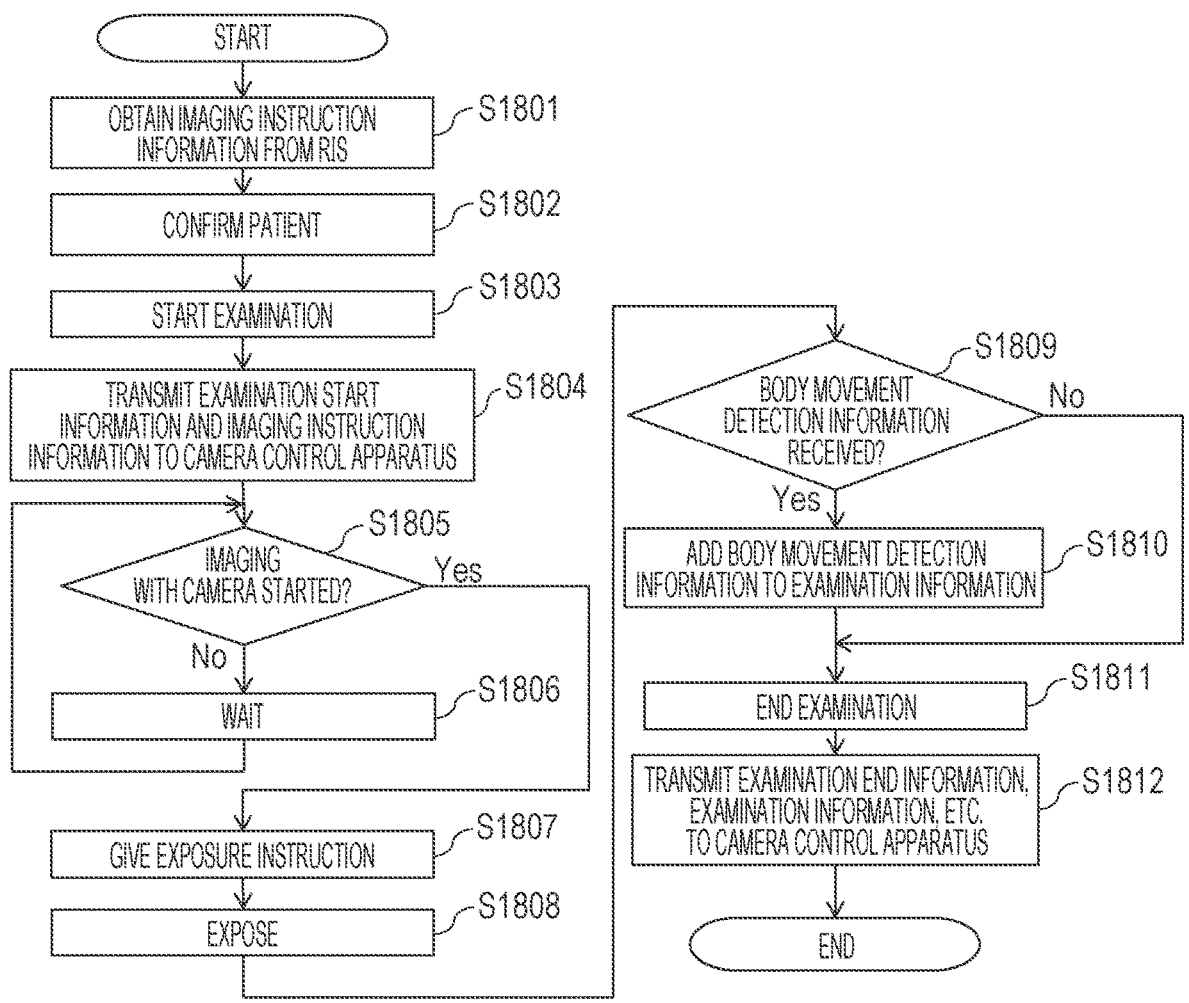
FIG. 18 illustrates the fifth embodiment of the present invention and is a flowchart illustrating an example of a processing procedure of a control method performed by the radiation imaging control apparatus illustrated in FIG. 1.

FIG. 18 illustrates the fifth embodiment of the present invention and is a flowchart illustrating an example of a processing procedure of a control method performed by the radiation imaging control apparatus 13 illustrated in FIG. 1.

When a radiographer operates the operation unit 132 of the radiation imaging control apparatus 13 to input an instruction to obtain examination information (including imaging instruction information) from the external system 20, the external system cooperating unit 134 obtains the examination information from the external system 20 in step S1801. Although the configuration of obtaining the examination information from the external system 20 is described in the present embodiment, a configuration in which a radiographer manually inputs the examination information via the operation unit 132 may be used, for example.

Subsequently, in step S1802, the radiographer confirms information (such as the patient ID and the patient name) regarding a patient who has come to the imaging room and guides the patient to the imaging location in the imaging room.

Thereafter, the radiographer gives an examination start instruction for an examination of the patient via the operation unit 132. Subsequently, in step S1803, for example, the control unit 133 detects this.

Subsequently, in response to the examination start instruction from the radiographer, the control unit 133 transmits information indicating that the examination has been started (circumstances in which the examination is performed) and the imaging instruction information of the corresponding examination to the camera control apparatus 15 in step S1804.

Subsequently, in step S1805, the control unit 133 performs communication with the camera control apparatus 15 and determines whether capturing of a camera moving image has been started by the camera apparatus 14.

If capturing of the camera moving image has not been started by the camera apparatus 14 yet as a result of the determination in step S1805 (S1805/No), the process proceeds to step S1806.

After the process proceeds to step S1806, the control unit 133 waits for a predetermined time. The process then returns to step S1805.

On the other hand, if capturing of the camera moving image has been started by the camera apparatus 14 as a result of the determination in step S1805 (S1805/Yes), the process proceeds to step S1807.

After the process proceeds to step S1807, the control unit 133 instructs the radiation generating apparatus 11 to expose the patient to radiation in response to the start of imaging instructed by the radiographer.

The radiation generating apparatus 11 that has received the radiation exposure instruction from the control unit 133 in step S1807 exposes the patient serving as an object to radiation in step S1808. Thereafter, the radiation detecting apparatus 12 detects, as an image signal (radiation image signal), radiation that is emitted from the radiation generating apparatus 11 and that is incident thereto, generates a radiation imaging image based on this radiation image signal, and outputs the generated radiation imaging image to the radiation imaging control apparatus 13.

Subsequently, in step S1809, the control unit 133 determines whether body movement detection information has been received from the camera control apparatus 15.

If the body movement detection information has been received from the camera control apparatus 15 as a result of the determination in step S1809 (S1809/Yes), the process proceeds to step S1810.

After the process proceeds to step S1810, the control unit 133 performs processing of adding the body movement detection information received in step S1809 to the examination information obtained in step S1801. Note that the examination information to which the body movement detection information is added may be any information. For example, when "detection date and time: 2017 Oct. 20 10:00, detection content: body movement" is received as the body movement detection information, "detection date and time: 2017 Oct. 20 10:00, detection content: body movement" may be added as failed image reason information included in the examination information as it is.

If the processing of S1810 ends or if it is determined in step S1809 that the body movement detection information has not been received from the camera control apparatus 15 (S1809/No), the process proceeds to step S1811.

After the process proceeds to step S1811, the control unit 133 obtains a radiation imaging image output from the radiation imaging control apparatus 13, and displays this radiation imaging image together with the body movement detection information on the display unit 131, for example. Then, the radiographer checks the body movement detection information and the radiation imaging image displayed on the display unit 131, and inputs an examination end instruction via the operation unit 132. The control unit 133 then detects this. Note that a configuration may also be adopted in which the radiographer inputs an instruction to perform the examination again after checking the body movement detection information and the radiation imaging image displayed on the display unit 131 and the process returns to step S1803 if the examination is performed again.

If the examination is ended without performing the examination again, the process proceeds to step S1812, in which the control unit 133 transmits information indicating that the examination has been ended (circumstances in which the examination is performed), the examination information, and the radiation imaging image to the camera control apparatus 15.

After the processing of step S1812 ends, the process of the flowchart illustrated in FIG. 18 ends.

Figure 19:
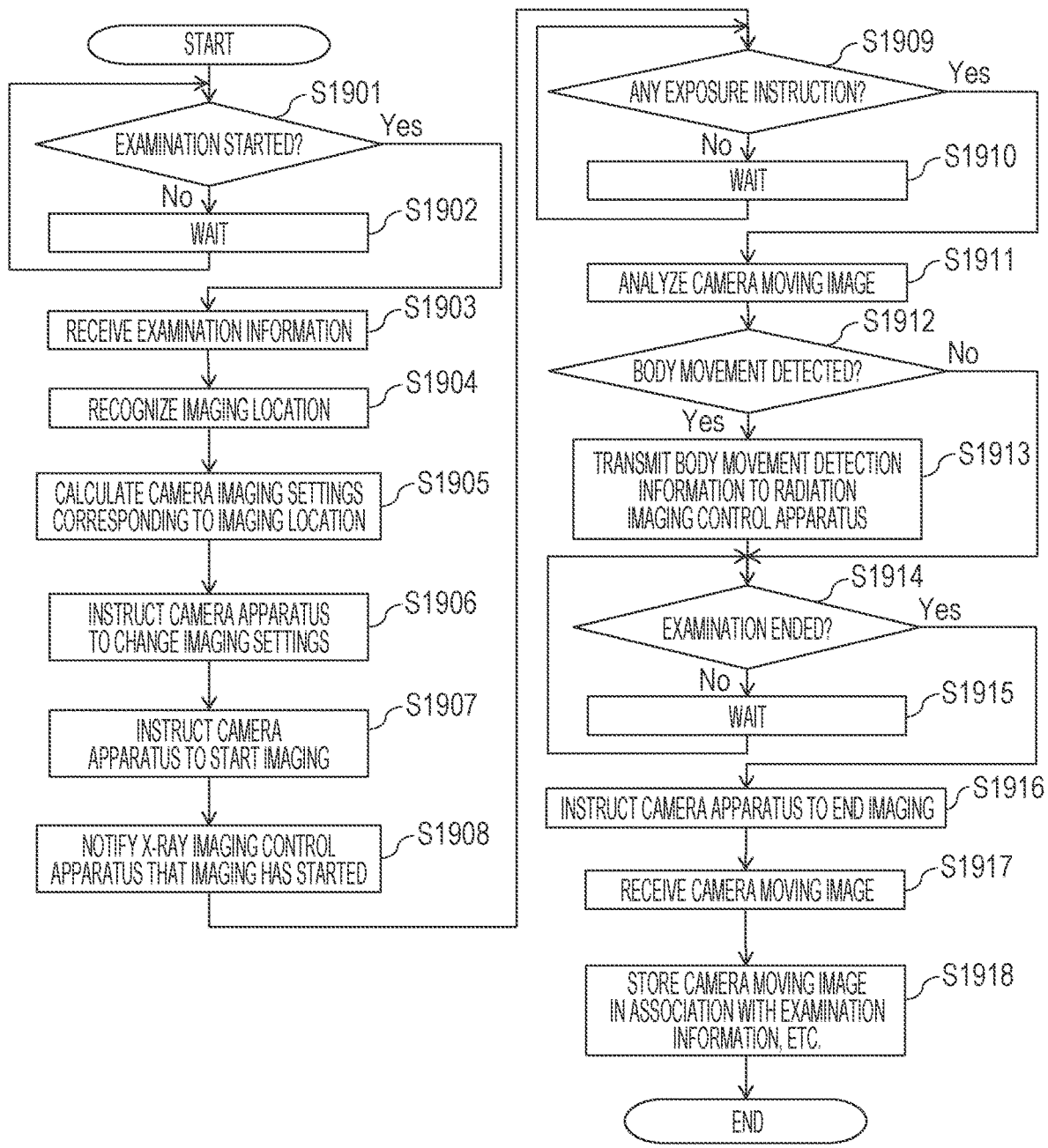
FIG. 19 illustrates the fifth embodiment of the present invention and is a flowchart illustrating an example of a processing procedure of a control method performed by the camera control apparatus illustrated in FIG. 1.

FIG. 19 illustrates the fifth embodiment of the present invention and is a flowchart illustrating an example of a processing procedure of a control method performed by the camera control apparatus 15 illustrated in FIG. 1.

First, in step S1901, the control unit 153 determines whether an examination start notification has been received from the radiation imaging control apparatus 13.

If the examination start notification has not been received from the radiation imaging control apparatus 13 yet as a result of the determination in step S1901 (S1901/No), the process proceeds to step S1902.

After the process proceeds to step S1902, the control unit 153 waits for a predetermined time. The process then returns to step S1901.

On the other hand, if the examination start notification has been received from the radiation imaging control apparatus 13 as a result of the determination in step S1901 (S1901/Yes), the process proceeds to step S1903.

After the process proceeds to step S1903, the communication unit 158 receives, after the start of examination, examination information (including imaging instruction information) of the corresponding examination from the radiation imaging control apparatus 13.

Subsequently, in step S1904, the imaging location recognizing unit 151 recognizes the imaging location at which radiation imaging is performed in the imaging room on the basis of the imaging instruction information included in the examination information received in step S703. The processing of the flowchart illustrated in FIG. 9 or the processing of the flowchart illustrated in FIG. 11 may be used as the detailed processing of this imaging location recognition processing in step S1904.

Subsequently, in step S1905, the imaging setting calculating unit 152 calculates settings of the camera apparatus 14 (for example, imaging settings such as the direction (orientation) and the imaging magnification of the camera apparatus 14) in accordance with the imaging location recognized in step S1904. Note that when the imaging magnification is calculated, for example, the magnification with which the imaging location recognized in step S1904 becomes the sharpest may be selected, the magnification with which the entire radiation detecting apparatus 12 is included in the imaging range may be selected, or the magnification with which the patient's face is included in the imaging range may be selected.

Subsequently, in step S1906, the control unit 153 instructs the camera apparatus 14 to change the settings of the camera apparatus 14 to the settings (imaging settings) calculated in step S1905.

Subsequently, in step S1907, the control unit 153 instructs the camera apparatus 14 to start imaging.

Subsequently, in step S1908, the control unit 153 notifies the radiation imaging control apparatus 13 that the camera apparatus 14 has started imaging.

Subsequently, in step S1909, the control unit 153 determines whether an exposure instruction (S1807) has been received from the radiation imaging apparatus 13.

If the exposure instruction has not been received from the radiation imaging apparatus 13 yet as a result of the determination in step S1909 (S1909/No), the process proceeds to step S1910.

After the process proceeds to step S1909, the control unit 153 waits for a predetermined time. The process then returns to step S1909.

On the other hand, if the exposure instruction has been received from the radiation imaging apparatus 13 as a result of the determination in step S1909 (S1909/Yes), the process proceeds to step S1911.

After the process proceeds to step S1911, the body movement detecting unit 1510 analyzes the camera moving image obtained by the camera apparatus 14 to determine whether body movement of a patient serving as an object is detected. At this time, a configuration may be adopted in which the body movement detecting unit 1510 detects body movement of the patient using any publicly known image recognition technique.

Subsequently, in step S1912, the body movement detecting unit 1510 determines whether body movement of the patient is detected as a result of the analysis performed in step S1911.

If body movement of the patient is detected as a result of the determination in step S1912 (S1912/Yes), the process proceeds to step S1913.

After the process proceeds to step S1913, the communication unit 158 transmits body movement detection information to the radiation imaging control apparatus 13. Note that the body movement detection information transmitted here may be any information. For example, the detection date and time and content of detection (for example, detection of body movement) may be transmitted as the body movement detection information.

If the processing of step S1913 ends or if body movement of the patient is not detected in step S1912 (S1912/No), the process proceeds to step S1914. After the process proceeds to step S1914, the control unit 153 performs communication with the radiation imaging control apparatus 13 to determine whether an examination end notification has been received from the radiation imaging control apparatus 13.

If the examination end notification has not been received from the radiation imaging control apparatus 13 yet as a result of the determination in step S1914 (S1914/No), the process proceeds to step S1915.

After the process proceeds to step S1915, the control unit 153 waits for a predetermined time. The process then returns to step S1914.

On the other hand, if the examination end notification has been received from the radiation imaging control apparatus 13 as a result of the determination in step S1914 (S1914/Yes), the process proceeds to step S1916.

After the process proceeds to step S1916, the control unit 153 instructs the camera apparatus 14 to end imaging in response to the end of the examination.

Subsequently, in step S1917, the moving image managing unit 155 receives a camera moving image captured by the camera apparatus 14 from the camera apparatus 14.

Subsequently, in step S1918, the moving image managing unit 155 stores, as camera moving image management information, the camera moving image received in step S1917 and the examination information (including the imaging instruction information) received in step S1903 in association with each other. At this time, the moving image managing unit 155 may obtain the radiation imaging image from the radiation imaging control apparatus 13, and may further store, as the camera moving image management information, the obtained radiation imaging image in association with the camera moving image and the examination information that are described above.

After the processing of step S1918 ends, the process of the flowchart illustrated in FIG. 19 ends.

Note that the functional configuration of the camera control apparatus 15 according to the fifth embodiment illustrated in FIG. 17 is a configuration further including the body movement detecting unit 1510 in addition to the functional configuration of the camera control apparatus 15 according to the first embodiment illustrated in FIG. 1. However, the present invention is not limited to this configuration. For example, the functional configuration of the camera control apparatus 15 according to the fifth embodiment may be a configuration further including the body movement detecting unit 1510 in addition to the functional configuration of the camera control apparatus 15 according to the fourth embodiment illustrated in FIG. 14. Such a configuration may also be encompassed by the present invention. When such a configuration is adopted, the configuration further including the camera selecting unit 159 illustrated in FIG. 14 in addition to the functional configuration illustrated in FIG. 17 is adopted.

The camera control apparatus 15 according to the fifth embodiment performs detection of body movement of a patient serving as an object from a camera moving image obtained by the camera apparatus 14 (S1912, S1913) in addition to the processing performed by the camera control apparatus 15 according to the first embodiment described above.

Such a configuration enables a radiographer to be informed of body movement of a patient serving as an object, which may become a cause of a failed image in radiation imaging, in addition to the advantageous effects of the first embodiment described above.

The present invention enables a camera apparatus to record an appropriate video image relating to circumstances in which radiation imaging is performed in an imaging room.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging system comprising:
a radiation generating apparatus configured to generate radiation toward an object;
a radiation detecting apparatus configured to detect the radiation as an image signal;
a camera apparatus configured to record an image relating to circumstances in which radiation imaging is performed using the radiation by the radiation detecting apparatus in an imaging room; and
a camera control apparatus configured to control the camera apparatus, wherein
the camera control apparatus includes at least one processor and at least one memory storing instructions, when executed by the at least one processor, cause the camera control apparatus to function as:
a recognition unit configured to recognize an imaging location at which the radiation imaging is performed, and
a setting unit configured to set a parameter of the camera apparatus in accordance with the imaging location recognized by the recognition unit,
the recognition unit recognizes the imaging location based on information, relating to the circumstances, in which the radiation imaging is performed, included in the image recorded by the camera apparatus.

2. The radiation imaging system according to claim 1, wherein the recognition unit performs processing of detecting the radiation detecting apparatus from the image and recognizes the imaging location in accordance with a result of the detection.

3. The radiation imaging system according to claim 2, wherein the recognition unit performs the processing of detecting the radiation detecting apparatus by detecting a marker attached to the radiation detecting apparatus.

4. The radiation imaging system according to claim 2, wherein the recognition unit performs recognition for setting the imaging location to a position of an imaging portion of the object in a case where the radiation detecting apparatus is successfully detected and performs recognition for setting the imaging location to a default position in a case where the radiation detecting apparatus is not successfully detected.

5. The radiation imaging system according to claim 2, wherein the recognition unit further performs processing of detecting an imaging portion of the object included in received information relating to the radiation imaging, performs recognition for setting the imaging location to a position of the imaging portion in a case where the radiation detecting apparatus is successfully detected and where the imaging portion is successfully detected, and performs recognition for setting the imaging location to a default position in a case where the radiation detecting apparatus is not successfully detected or in a case where the radiation detecting apparatus is successfully detected but the imaging portion is not successfully detected.

6. The radiation imaging system according to claim 1, wherein the recognition unit performs processing of detecting the object from the image and recognizes the imaging location in accordance with a result of the detection.

7. The radiation imaging system according to claim 6, wherein the recognition unit performs recognition for setting the imaging location to a position of the object in a case where the object is successfully detected and performs recognition for setting the imaging location to a default position in a case where the object is not successfully detected.

8. The radiation imaging system according to claim 7, wherein the recognition unit further performs processing of detecting an imaging portion of the object included in received information relating to the radiation imaging, performs recognition for setting the imaging location to a position of the imaging portion in a case where the imaging portion is successfully detected, and performs recognition for setting the imaging location to a position of the object in a case where the imaging portion is not successfully detected.

9. A radiation imaging system comprising:
a radiation generating apparatus configured to generate radiation toward an object;
a radiation detecting apparatus configured to detect the radiation as an image signal;
a camera apparatus configured to record an image relating to circumstances in which radiation imaging is performed using the radiation by the radiation detecting apparatus in an imaging room; and
a camera control apparatus configured to control the camera apparatus,
a radiation imaging control apparatus configured to control the radiation generating apparatus and the radiation detecting apparatus,
wherein the camera control apparatus includes at least one processor and at least one memory storing instructions, when executed by the at least one processor, cause the camera control apparatus to function as:
a recognition unit configured to recognize an imaging location at which the radiation imaging is performed, and
a setting unit configured to set a parameter of the camera apparatus in accordance with the imaging location recognized by the recognition unit, the recognition unit recognizes the imaging location based on information relating to an imaging condition transmitted from the radiation imaging control apparatus.

10. The radiation imaging system according to claim 9, wherein the at least one memory storing instructions, when executed by the at least one processor, cause the camera control apparatus to further function as:
a management unit configured to manage the image and the information transmitted from the radiation imaging control apparatus in association with each other.

11. The radiation imaging system according to claim 9, further comprising
a plurality of the camera apparatuses, wherein the at least one memory storing instructions, when executed by the at least one processor, cause the camera control apparatus to further function as:
a selecting unit configured to select one camera apparatus from among the plurality of camera apparatuses, based on the information transmitted from the radiation imaging control apparatus.

12. The radiation imaging system according to claim 9, wherein the radiation imaging control apparatus includes at least one processor and at least one memory storing instructions, when executed by the at least one processor, cause the radiation image control apparatus to function as:
a cooperating unit configured to cooperate with an external system and obtain information relating to the radiation imaging from the external system, and
a control unit configured to perform control to transmit the information obtained by the cooperating unit to the camera control apparatus.

13. The radiation imaging system according to claim 1, wherein the at least one memory storing instructions, when executed by the at least one processor, cause the camera control apparatus further functions as:
a body movement detection unit configured to detect body movement of the object from the image, and
a communication unit configured to transmit, in a case where body movement of the object is detected by the body movement detection unit, body movement detection information to a radiation imaging control apparatus configured to control the radiation generating apparatus and the radiation detecting apparatus.

14. A camera control apparatus configured to control a camera apparatus configured to record an image relating to circumstances in which radiation imaging is performed using a radiation detecting apparatus that images an object by emitted radiation in an imaging room, comprising:
at least one processor; and
at least one memory storing instructions, when executed by the at least one processor, cause the camera control apparatus to function as:
a recognition unit configured to recognize an imaging location at which the radiation imaging is performed in the imaging room; and
a setting unit configured to set a parameter of the camera apparatus in accordance with the imaging location recognized by the recognition unit,
the recognition unit recognizes the imaging location based on information, relating to the circumstances, in which the radiation imaging is performed, included in the image recorded by the camera apparatus.

15. A control method of controlling a camera apparatus configured to record an image relating to circumstances in which radiation imaging is performed using a radiation detecting apparatus that images an object by emitted radiation in an imaging room, comprising:
recognizing an imaging location at which the radiation imaging is performed in the imaging room; and
setting a parameter of the camera apparatus in accordance with the imaging location recognized in the recognizing,
in the recognizing, the imaging location is recognized based on information, relating to the circumstances, in which the radiation imaging is performed, included in the image recorded by the camera apparatus.

16. A radiation imaging system comprising:
a radiation generating apparatus;
a radiation detecting apparatus configured to detect radiation as an image signal;
a camera apparatus configured to image circumstances in which radiation imaging is performed by the radiation detecting apparatus; and
a camera control apparatus configured to control the camera apparatus,
wherein the camera control apparatus includes at least one processor and at least one memory storing instructions, when executed by the at least one processor, cause the camera control apparatus to function as:
a recognition unit configured to recognize an imaging location at which the radiation imaging is performed, and
a setting calculating unit configured to calculate settings of the camera apparatus in accordance with the imaging location recognized by the recognition unit,
the recognition unit recognizes the imaging location based on information relating to the circumstances, in which the radiation imaging is performed, imaged by the camera apparatus.

* * * * *